United States Patent [19]
Bobo, Sr.

[11] Patent Number: 5,573,007
[45] Date of Patent: Nov. 12, 1996

[54] GAS COLUMN PRESSURE MONITORING CATHETERS

[75] Inventor: Donald E. Bobo, Sr., Fountain Valley, Calif.

[73] Assignee: Innerspace, Inc., Santa Ana, Calif.

[21] Appl. No.: 287,195

[22] Filed: Aug. 8, 1994

[51] Int. Cl.⁶ .................................................. A61B 5/00
[52] U.S. Cl. .................................... 128/748; 128/774
[58] Field of Search ............................... 128/748, 774, 128/775, 778, 780, 673

[56] References Cited

U.S. PATENT DOCUMENTS

| | | | |
|---|---|---|---|
| 2,840,069 | 9/1958 | Squire et al. | 128/2 |
| 4,227,420 | 10/1980 | Lamadrid | 73/756 |
| 4,300,571 | 11/1981 | Waldbilling | 128/673 |
| 4,314,480 | 2/1982 | Becker | 73/706 |
| 4,413,528 | 11/1983 | Hok et al. | 128/673 |
| 4,543,965 | 10/1985 | Pack et al. | 128/748 |
| 4,648,406 | 3/1987 | Miller | 128/674 |
| 4,672,974 | 6/1987 | Lee | 128/673 |
| 4,809,710 | 3/1989 | Williamson | 128/748 |
| 4,841,984 | 6/1989 | Armeniades et al. | 128/748 |
| 4,981,470 | 1/1991 | Bombeck | 128/642 |
| 5,105,820 | 4/1992 | Moriuchi et al. | 128/675 |
| 5,263,485 | 11/1993 | Hickey | 128/673 |
| 5,279,308 | 6/1994 | DiSabito et al. | 128/775 |

FOREIGN PATENT DOCUMENTS

| | | |
|---|---|---|
| 8200096 | 7/1986 | WIPO. |
| 860004 | 7/1986 | WIPO. |
| 90/01157 | 10/1990 | WIPO. |

OTHER PUBLICATIONS

"Device for Pressure Measurement", Hilgendorf et al. Jul. 1986 (English translation of Spiegelberg—PCT/DE86/00004).

Primary Examiner—Max Hindenberg
Attorney, Agent, or Firm—Stephen C. Shear

[57] ABSTRACT

A gas-column pressure measuring catheter which is insertable into a mammalian body for purposes of transmitting pressure changes from a location within the mammalian body to a pressure sensor which is either incorporated into, or connected to, the catheter. In a preferred embodiment, the gas-column pressure measuring catheter comprises an elongate catheter body having a gas-filled lumen extending longitudinally therethrough, and a gas-filled membrane-walled chamber positioned on the catheter body in communication with the gas-filled lumen such that pressure changes exerted against the outer surface of the membrane-walled chamber will result in the transmission of pressure changes through the gas-filled catheter lumen. The gas-filled membrane-walled chamber may be located on the side wall of the catheter body, or may be located on the distal end of the catheter body. The invention includes methods for measuring various intracorporeal pressures using gas-column pressure measuring catheters, including methods for measuring blood pressure, intracranial pressure, intrauterine pressure, pulmonary artery pressures, and other intravascular or intracomparmental pressures. The invention also provides means and methods for replenishing gas lost by diffusion out of the membrane-walled chamber,

55 Claims, 7 Drawing Sheets

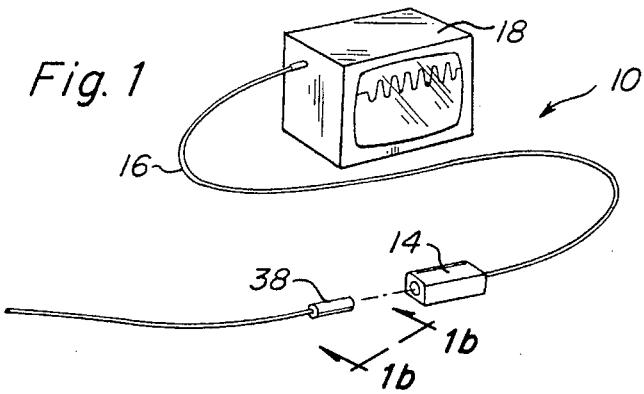
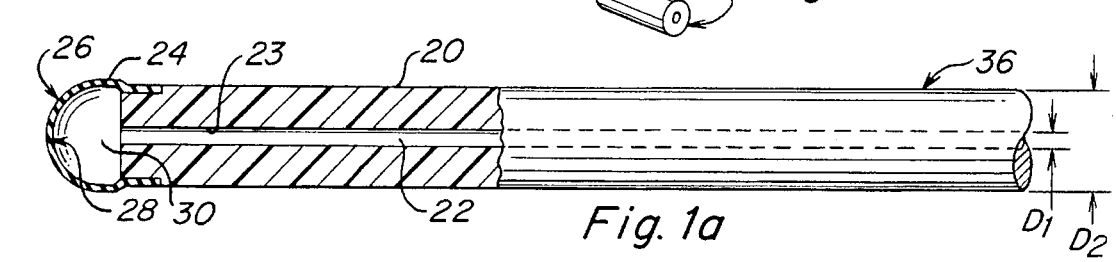
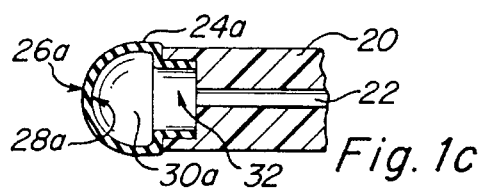
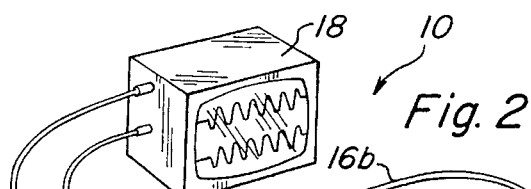
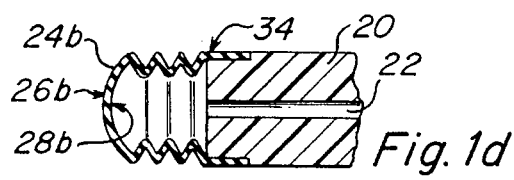
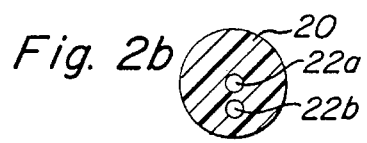
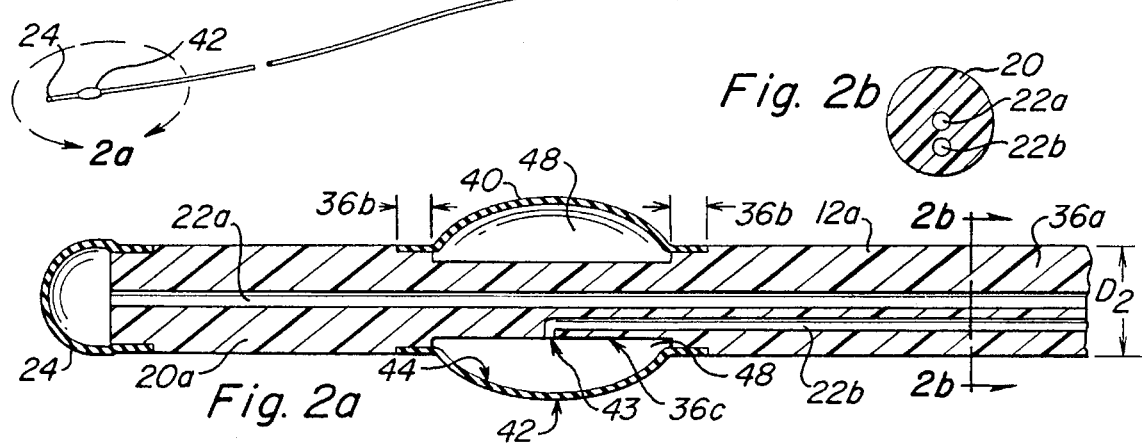

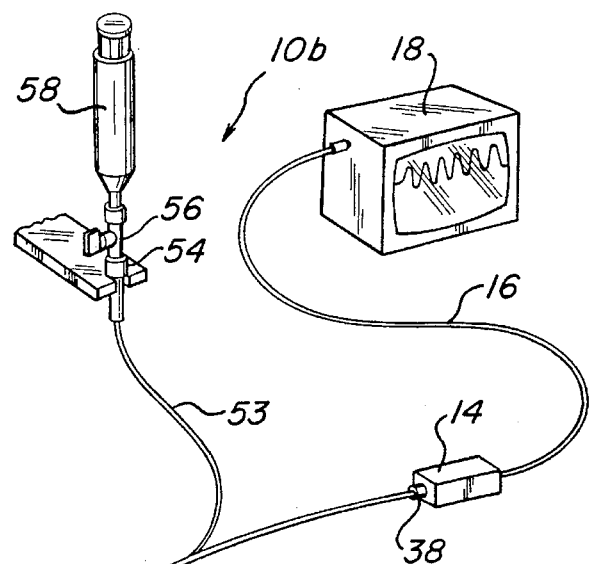
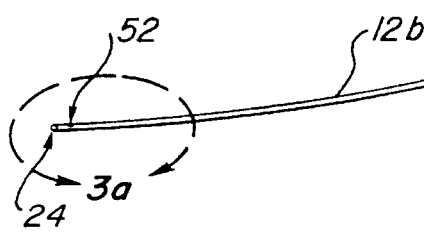
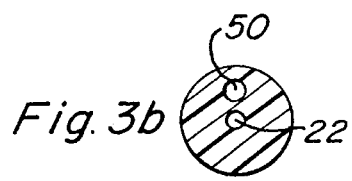
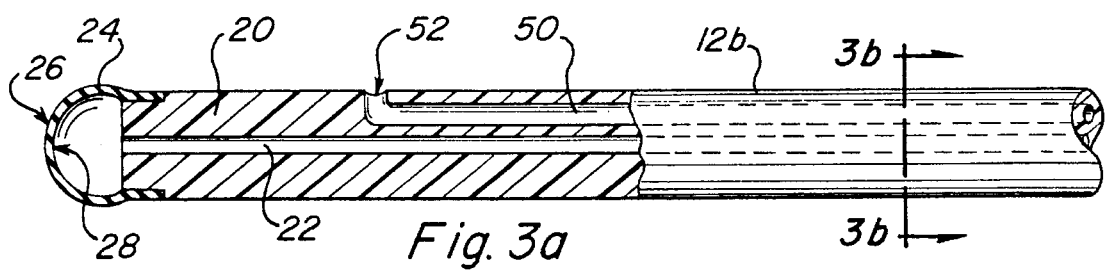
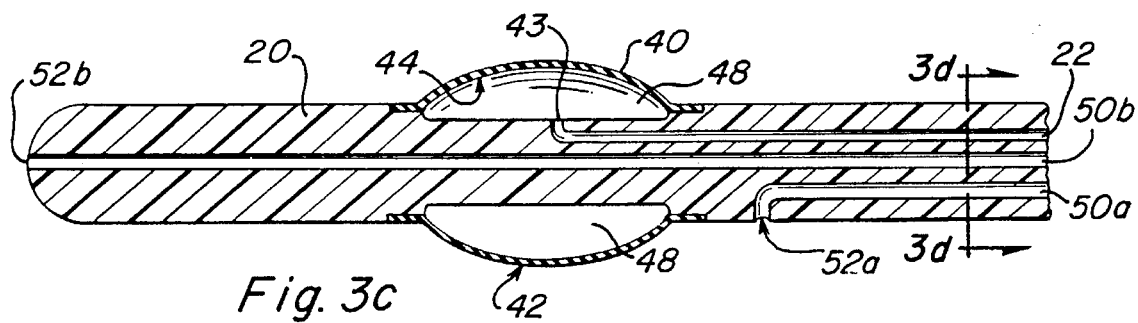
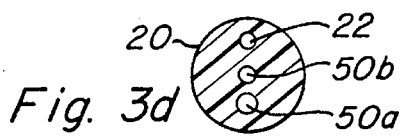

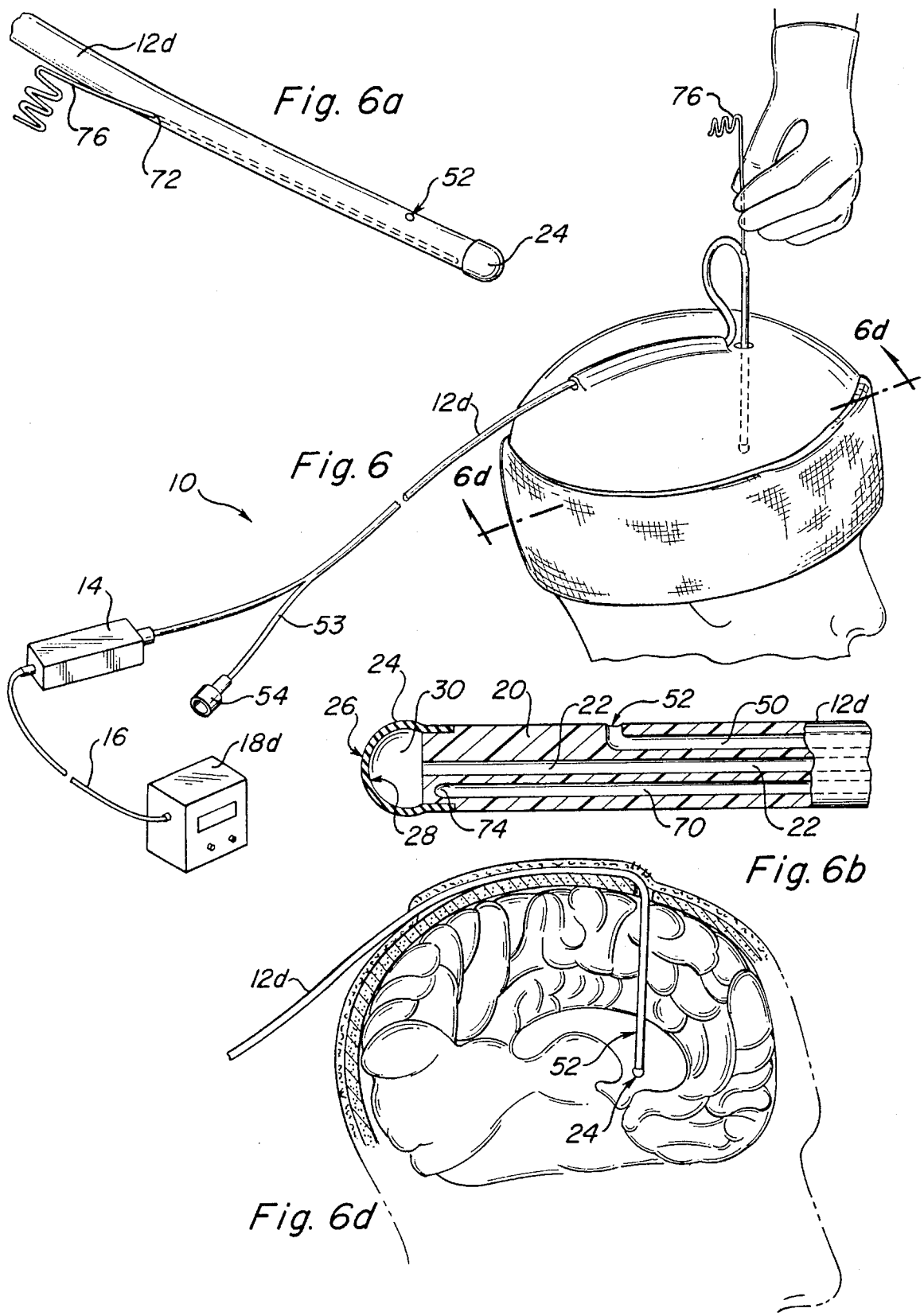

GAS COLUMN PRESSURE MONITORING CATHETERS

FIELD OF THE INVENTION

The present invention pertains generally to medical equipment and more particularly to air filled catheter systems for monitoring pressures within blood vessels and other anatomical passageways/cavities of a mammalian body.

BACKGROUND OF THE INVENTION

A. Prior Art Methods of Physiological Pressure Monitoring By Liquid-Column Catheters Clinically, it has heretofore been common practice to utilize liquid-filled tubular pressure monitoring catheters for measuring pressures within anatomical passageways, organs, compartments and cavities of the mammalian body. Typically, such medical pressure monitoring catheters comprise elongate tubular catheters having one or more hollow lumens extending longitudinally therethrough, and one or more openings near the distal end of the catheter through which pressure changes in the surrounding medium are received into the catheter lumen(s). The proximal end of the catheter is typically connected to a physiological pressure transducer and the transducer and catheter lumen(s) are charged with a liquid (e.g., saline solution) through which changes in pressure are transmitted from the distal end of the catheter, to the extracorporeally located pressure transducer. The pressure transducer converts received changes in pressure to electrical signals which may be transmitted to a corresponding display apparatus (e.g., a bedside monitor) or recording apparatus (e.g., magnetic tape, chart recorder).

Liquid filled pressure monitoring catheters of the above-described type have been used to monitor various pressures within the mammalian body, including arterial pressure, central venous pressure, pulmonary artery pressures, pressures within the chambers of the heart, intracranial pressure, intrauterine pressure during labor & delivery etc...

In most physiological pressure monitoring applications using liquid filled catheters, it is necessary to maintain sterility of the liquid-filled catheter, the pressure transmitting liquid and all of the portions of the pressure transducer which come into contact with the pressure transmitting liquid so as to avoid the introduction of pathogenic organisms into the body. Also, in many long term clinical applications, it is necessary to provide a continuous or periodic flow of liquid (e.g., heparinized saline solution) through the catheter to prevent occlusion (e.g., the formation of blood clots) of the catheter lumen and to maintain patency of the catheter. In applications such as arterial pressure monitoring or central venous pressure monitoring, it is common practice to employ a constant flush apparatus such as that commercially available as Model No 42684-05, available from Abbott Laboratories, Chicago, Ill., in conjunction with the pressure monitoring catheter to maintain a slow continuous flow of heparinized saline solution or other liquid through the catheter. Such constant flush apparatus must maintain the flow of liquid at a sufficiently low level as to avoid interference with the pressure monitoring function of the catheter. The utilization of such constant flushing apparatus adds to the overall expense of the pressure monitoring catheter system.

Additionally, during set up of a liquid-filled pressure monitoring catheter of the prior art, it is typically necessary to prime the catheter with a sterile liquid and to carefully remove any air bubbles which form within the catheter or transducer, as the presence of such air bubbles may adversely affect the responsiveness of the transducer. Thereafter, while the catheter remains inserted, any inadvertent introduction of air bubbles during flushing or manipulation of the transducer/catheter may result in damping of dynamic response of the system. Such damping may result in inaccuracy of the monitored pressure, especially in applications wherein a continuous pressure wave form is to be monitored (e.g., arterial pressure monitoring).

Additionally, when using the liquid filled pressure monitoring catheters of the prior art, it is typically necessary to make certain that the pressure transducer is on a level plane with the pressure-receiving aperture(s) of the catheter to avoid inducement of hydrostatic error in the monitored pressure. After the transducer has been leveled with the catheter, any movement or adjustment of the positioning of the patient will result in a hydrostatic error in the pressure reading obtained, unless the pressure transducer is correspondingly relieved.

B. Prior Art Devices Which Measure Physiological Pressure Transmitted Through a Gaseous Medium The following United States and foreign patents/patent publications have described pressure measuring catheters, and other pressure transmitting systems, wherein a gas is utilized as a pressure-transmitting medium in at least a portion of the systems: U.S. Pat. Nos. 2,840,069 (Squire, et al.), 4,227,420 (Lamadrid), 4,300,571 (Waldbilling), 4,314,480 (Becker), 4,648,406 (Miller), 4,841,984 (Armeniades et al.), 5,105,820 (Moriuchi, et al.), 5,279,308 (DiSabito, et al.); Foreign Patent publications: WO82/02657 (Ebert), WO86/03957 (Spiegelberg), WO90/11717 (Utah Medical Prod., Inc.).

In particular, WO86/03957 (Speigelberg) describes a medical pressure monitoring catheter having a gas-filled lumen extending longitudinally therethrough and in gaseous communication with the inflation space of a partially inflated bag. Changes in pressure against the outer surface of the bag are transmitted through the gas-filled lumen of the catheter to an externally located pressure sensor. An electromechanical pump system is utilized to provide the desired degree of bag inflation to facilitate the intended pressure monitoring function of the catheter.

Although the prior art has included at least one gas-column pressure monitoring catheter and a number of other devices which utilize gas as a pressure transmitting medium, there remains a need in the art for the development of new pressure monitoring catheters which utilize gas, rather than liquid, as the pressure-transmitting medium and which are designed constructed and configured to avoid some or all of the problems, sterility requirements and/or limitations associated with the prior art pressure monitoring catheters.

SUMMARY OF THE INVENTION

The present invention is a gas-column pressure measuring catheter which is insertable into a mammalian body, and usable to transmit pressure changes from a location within the mammalian body to a pressure sensor which is either incorporated into, or connectable to, the catheter. The catheter comprises an elongate flexible catheter body having a gas filled lumen extending longitudinally through at least a portion of said catheter body. At least one gas-filled membrane-walled chamber is formed on the catheter body, in fluidic communication with said gas filled lumen. Such gas-filled chamber is at least partially defined or bounded by a flaccid membrane 24, 40. Such membrane 24, 40 is positioned and configured such that pressure exerted against the outer surface of the membrane 24, 40 will cause the membrane 24, 40 to compress or move inwardly, thereby increasing the pressure of the gas within the gas-filled chamber and associated catheter lumen. A subsequent decrease in the pressure exerted against the outer surface of the membrane 24, 40 will allow the membrane 24, 40 to decompress or move outwardly, thereby lowering the pressure of the gas within the chamber and lumen.

The catheter lumen is connectable to, or may incorporate, a pressure sensor which is operative to sense the changes in gas pressure within the catheter lumen. The pressure sensor emits electrical signals in response to such changes in gas pressure within the catheter lumen indicative of the magnitude of pressure changes against the outer surface of the flaccid wall or membrane 24, 40. The pressure sensor may be connectable to a monitor or other pressure displaying or recording apparatus to permit monitoring or recordation of the sensed pressure changes.

In accordance with the invention, the flaccid membrane 24, 40 which defines or bounds at least a portion of the gas filled chamber may be in the form of a bulbous flaccid membrane 24 mounted on the distal end of the catheter body. Alternatively, the flaccid membrane 40 may be of an annular, cylindrical or other configuration and mounted on the sidewall of the catheter body at some location between the proximal and distal ends thereof.

The gas column pressure measuring catheters of the present invention may incorporate one or more working lumens, separate and apart from the gas-filled pressure monitoring lumen(s), which extend longitudinally through the catheter body and terminate in one or more infusion/withdrawal apertures, to permit infusion and/or withdrawal of liquids or other substances through the catheter.

The gas-column pressure monitoring catheters of the present invention may be specifically configured and equipped for specific pressure monitoring applications. For example, the catheter of the present invention may be specifically configured as a right-heart pulmonary artery catheter (e g., "Swan-Ganz" catheter) In accordance with this embodiment of the invention, the catheter may comprise an elongate flexible catheter body having at least a first gas-filled pulmonary artery pressure monitoring lumen which extends longitudinally through the catheter body and terminates in a gas-filled membrane-walled pulmonary artery pressure monitoring chamber at the distal end of the catheter body. A pulmonary artery occlusion or wedge balloon is positioned near the distal tip of the catheter and, when inflated, will occlude blood flow through the pulmonary artery in which the catheter is located, thereby facilitating a measurement of pulmonary artery wedge pressure by the gas-filled membrane-walled pressure sensing chamber on the distal end of the catheter body. Optionally, a thermistor system may be incorporated within the body of the catheter to facilitate the measurement of cardiac output by known thermal dilution methodology. Also, an optional thermal dilution injectate lumen may extend from the proximal end of the catheter body to an injectate port located on the portion of the catheter body which resides in the vena cava or right atrium of the heart to facilitate injection of a desired thermal dilution injectate for accomplishing cardiac output measurement. Additionally, an optional blood sample withdrawal lumen may extend through the catheter body, terminating in a blood withdrawal port near the distal end thereof, to facilitate withdrawal of mixed venous blood samples from the pulmonary artery. Additionally, an optional second gas-filled lumen may extend from the proximal end of the catheter body to a second gas-filled membrane-walled pressure monitoring chamber located on the catheter body at a location which will reside in the vena cava thereby facilitating the monitoring of central venous pressure.

A gas-column pressure monitoring catheter of the present invention may be specifically constructed and configured for use as an intracranial pressure monitoring catheter. In accordance with this aspect of the invention, the device will comprise an elongate flexible catheter body having at least one gas-filled lumen extending longitudinally therethrough in communication with at least one gas-filled, membrane-wall pressure monitoring chamber of the foregoing character, positioned at or near the distal end of the catheter body. An optional blind stylet-receiving lumen may extend distally through the catheter body, from a stylet entry aperture located a spaced distance from the distal end of the catheter body, to a blind end point located near or substantially coterminous with the distal end of the catheter body. A stiffening stylet, such as a wire, is insertable through the stylet entry aperture, and advanceable into the stylet lumen to a point where the distal end of the stylet abuts against the blind endpoint of the stylet lumen. In this manner, the stylet will serve to stiffen only a distal portion of the catheter body, and will facilitate intracranial insertion of the catheter by way of a known scalp tunnel technique. Additionally, the intracranial pressure monitoring embodiment of the catheter may comprise one or more hollow lumens extending throughout he catheter body for venting or allowing outflow of excess cerebral spinal fluid, thereby preventing the buildup of excessive intracranial pressure.

A gas-column pressure monitoring catheter of the present invention may be specifically configured and constructed for use as a central venous pressure monitoring catheter. In accordance with this aspect of the invention, the catheter may comprise an elongate flexible catheter body having a gas-filled central venous pressure monitoring lumen extending longitudinally through the catheter body and communicating with a gas-filled membrane-walled pressure monitoring chamber. The gas-filled membrane-walled pressure monitoring chamber may be located on the distal tip of the catheter body, or may be located on the side wall of the catheter body. One or more separate working lumen(s), for infusion of fluids and/or withdrawal of blood samples, extends through the catheter body and terminates in at least one infusion/withdrawal aperture located at or near the distal end of the catheter body. By such arrangement, the catheter may be inserted and advanced to a point where the membrane-walled chamber is located in the vena cava or other locations suitable for monitoring of central venous pressure. While the catheter remains in such position, the working lumen(s) may be periodically or continuously utilized to infuse fluids and/or withdraw blood samples from the central venous circulation.

A gas column pressure monitoring catheter of the present invention may be specifically configured and constructed for use as an intrauterine pressure monitoring catheter. In accordance with this aspect of the invention the device will comprise an elongate flexible catheter body having one or more gas-filled lumens extending longitudinally therethrough in communication with one or more gas-filled membrane-wall pressure monitoring chambers of the types described hereabove. The provision of two or more gas-filled membrane-wall pressure monitoring chamber on the catheter body will permit the catheter to consistently monitor changes in intrauterine pressure, without require frequent repositioning of the catheter due to regionalized depletion or drainage of amniotic fluid.

Further, in accordance with the invention, it has been determined that disruption or distortion of pressure monitoring may occur due to formation of a liquid plug within the gas-filled lumen of the catheter as a result of water vapor passage through the membrane wall, and subsequent condensation in the region of the catheter which transitions from body temperature to room temperature. To counter this problem a moisture absorbing material or apparatus may be incorporated into, or utilized in connection with, the gas-filled pressure monitoring catheter to remove or absorb and hold any moisture which accumulates within the gas-filled pressure monitoring lumen of the catheter. In a presently preferred embodiment, such moisture absorbing material or apparatus may comprise a hygroscopic material disposed within, or coated upon the walls of at least that portion of the gas-filled pressure monitoring lumen where the catheter transitions from body temperatures to room temperature. Various other moisture-removing elements or apparatus may also be utilized. For example, a wicking thread or other absorbable strand may be positioned within the gas-filled pressure monitoring lumen, so as to continually absorb condensate and prevent such condensate from forming a liquid plug within the gas-filled pressure monitoring lumen.

Alternatively, in catheters wherein a distal portion of the catheter is intended to be inserted intracorporeally, while a proximal portion of the catheter remains exteriorized, a condensation inhibiting element may be utilized to prevent condensation of water vapor within the exteriorized proximal portion of the catheter due to the inherent lower temperature of the exteriorized proximal portion, relative to the intracorporeally inserted distal portion thereof. In accordance with this aspect of the invention, a heating apparatus may be incorporated into or applied to the proximal portion of the catheter for warming the proximal portion of the catheter to a temperature which is close enough to the temperature of the intracorporeally inserted distal portion of the catheter to prevent condensation of any water vapor which accumulates within the gas-filled lumen of the catheter during use.

Further in accordance with the invention there are provided apparatus and systems for passing make-up gas into the catheter lumen to replenish gas which is lost from the catheter during use. One manner in which gas may be lost from the catheter during use is through outward diffusion of gas through the flaccid membrane 24, 40 while the catheter remains indwelling within the mammalian body. In accordance with this aspect of the invention, a pressurizing apparatus such as a pump or diffusive gas infusing device may be connected to the catheter for purposes of providing a flow of make-up gas into the catheter lumen. The preferred diffusive make-up gas system of the present invention provides a diffusive flow of makeup gas at a rate which is substantially equal to the rate at which gas will diffuse outwardly through the flaccid membrane of the catheter, thereby maintaining the desired volume of gas within the catheter for an extended period of time.

Further objects, advantages and applications of the invention will become apparent to those skilled in the art upon reading the following detailed description, and upon consideration of the accompanying drawings.

BRIEF DESCRIPTION OF THE DRAWINGS

FIG. 1 is a perspective view of a first embodiment of a gas-column pressure monitoring catheter system of the present invention.

FIG. 1a is a partial longitudinal sectional view of the distal-most portion of the catheter shown in FIG. 1.

FIG. 1b is a perspective view of the proximal end of the catheter shown in FIG. 1.

FIG. 1c is a longitudinal sectional view of an alternative distal tip configuration showing an alternative construction of the gas-filled membrane-walled pressure monitoring chamber at the distal end of the catheter of FIG. 1.

FIG. 1d is a longitudinal sectional view of another alternative distal tip configuration having an alternative bellows-membrane walled pressure monitor chamber.

FIG. 2 is a perspective view of a second embodiment of a pressure monitoring catheter system of the present invention incorporating two (2) gas-filled lumens and two (2) gas-filled diaphragmatic pressure measuring chambers.

FIG. 2a is a longitudinal section view of the distal-most portion of the catheter of FIG. 2.

FIG. 2b is a cross sectional view through line 2b—2b of FIG. 2.

FIG. 3 is a perspective view of a third embodiment of a pressure monitoring catheter system of the present invention incorporating a separate liquidinfusion/aspiration lumen extending through the catheter body.

FIG. 3a is a longitudinal sectional view of the distal-most portion of the catheter of FIG. 3.

FIG. 3b is a cross sectional view through line 3b—3b of FIG. 3a.

FIG. 3c is a longitudinal sectional view of an alternative configuration of the distal-most portion of the catheter of FIG. 3.

FIG. 3d is a cross-sectional view through line 3d—3d of FIG. 3c.

FIG. 4 is a perspective view of a fourth embodiment of a perspective view of a fourth embodiment of a pressure monitoring catheter system of the present invention intended for insertion into a pulmonary artery, and incorporating multiple gas-filled lumens, multiple gas-filled membrane-walled pressure measuring chambers, a pulmonary artery occlusion balloon, a cardiac output measuring thermistor system and a sample withdrawal lumen for obtaining mixed venous blood samples from the pulmonary artery.

FIG. 4a is a longitudinal sectional view of a distal portion of the catheter of FIG. 4 which resides within a pulmonary artery during operative placement of the catheter.

FIG. 4b is a longitudinal section view of a central portion of the catheter of FIG. 4 intended to reside within the vena cava during operative placement of the catheter.

FIG. 4c is a cross sectional view through line 4d—4d of FIG. 4a.

FIG. 4d is a cross sectional view through line 4e—4e of FIG. 4b.

FIGS. 6 and 6a are perspective view of a fifth embodiment of a gas-filled pressure monitoring catheter system of the present invention usable for intracranial pressure monitoring.

FIG. 6b is a perspective view of the distal-most portion of the catheter of FIG. 6a having a removable stiffening stylet member positioned therein.

FIG. 6d is a cutaway view of the human cranium having the catheter of FIG. 6a operatively inserted into a ventricle of the brain by way of a scalp-tunnel insertion technique.

FIG. 7a is a longitudinal sectional view of the distal-most portion of the catheter.

DETAILED DESCRIPTION OF THE PREFERRED EMBODIMETNS

Figures 4, 4A, 4B, 4C, 4D:
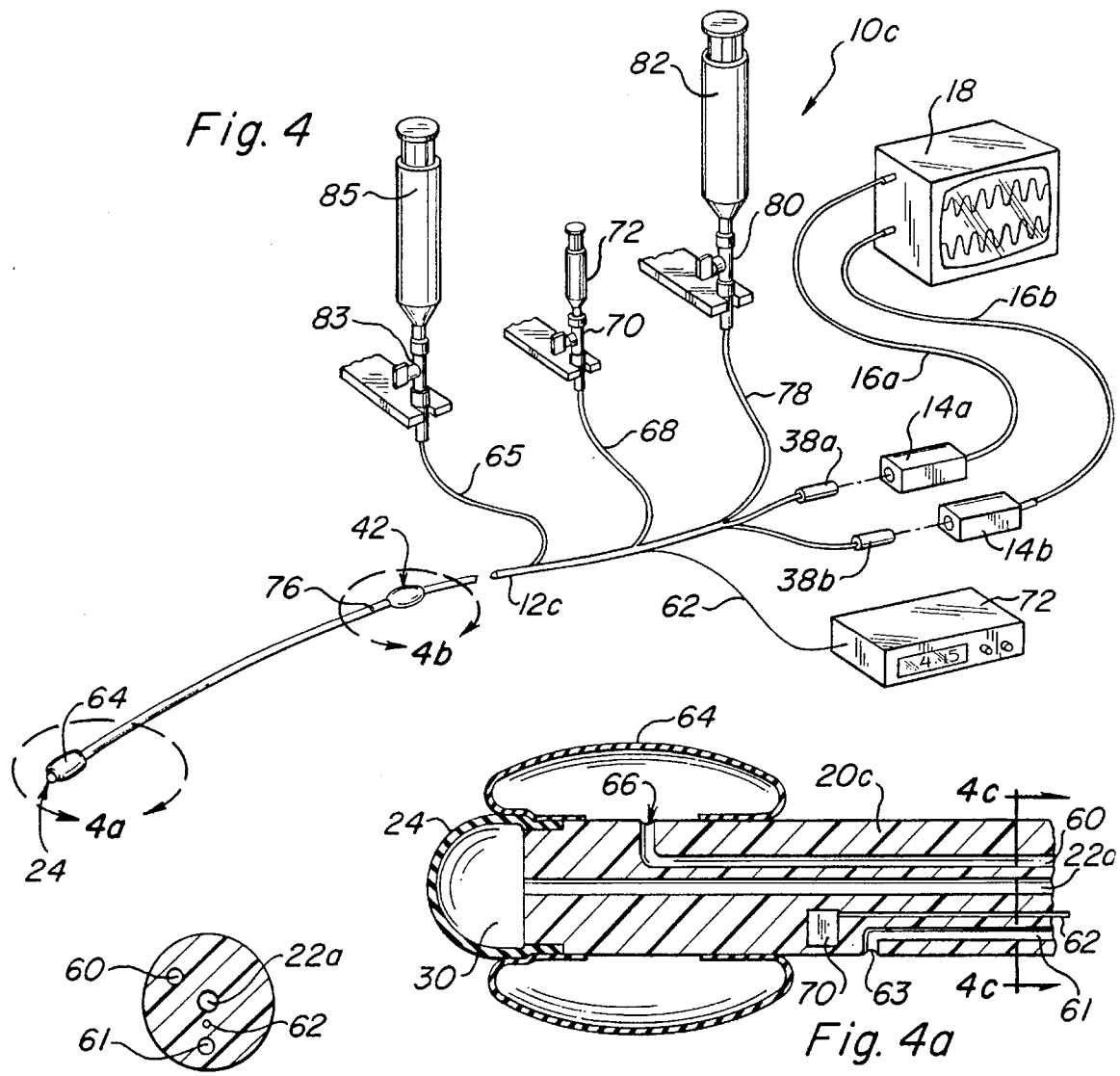

The following detailed description and the accompanying drawings are intended to describe and illustrate certain embodiments of the invention only and are not intended to function as a limitation of the scope of the invention, or to provide an exhaustive description of all embodiments in which the invention may take physical form.

i. Elements and Attributes Common To All Catheter Embodiments

Although the gas-column pressure monitoring catheters of the present invention may be constructed in various ways, including as the specific embodiments described herebelow, all embodiments of the invention do share certain basic attributes. In particular, all embodiments of the invention comprise an elongate (i.e., having a length greater than its width) catheter 12 having at least one gas-filled pressure monitoring lumen 22 extending longitudinally through at least a portion thereof. A gas-filled membrane-walled chamber 30, 48 is formed on the outer surface of the catheter 12, in gaseous communication with the gas-filled pressure monitoring lumen 22. By such arrangement, changes in pressure against the gas-filled membrane-walled chamber 30 will result in changes in pressure of the gas within the gas-filled pressure monitoring lumen 22. A pressure sensor 14 is connected to the proximal end of the gas-filled pressure monitoring lumen 22 to sense and display or record the changes in pressure which are communicated through the gas-filled pressure monitoring lumen 22 of the catheter 12. Alternatively, a pressure sensor may be mounted or incorporated into the catheter 12, or proximal connector 38 formed on the proximal end of the catheter 12. In such embodiments where a pressure sensor is actually incorporated into the catheter 12 or proximal connector 38 thereon the external pressure sensor 14 will not be required and the proximal end of the catheter 38 will be connected to the monitor 18 by way of a standard wiring or electrical connection of the type known in the art.

The gas-filled membrane-walled chamber 30, 48 of the catheter 12 has a flaccid membrane 24, 40 disposed thereon such that pressure exerted against the outer surface of the membrane 24, 40 causes the membrane to move or translate inwardly, thereby compressing the gas within the gas-filled chamber 30, 48 and lumen 22 of the catheter 12. When the pressure against the outer surface of the membrane 24, 40 is decreased, the membrane will move or translate outwardly, thereby lowering the pressure of gas within the chamber 30, 48 and lumen 22 of the catheter 12. The volume of gas within the lumen 22, relative to that within the chamber 30, 48 is sized to facilitate the desired pressure range of the pressure monitoring catheter 12. The lumen diameter is selected relative the lumen length to achieve the desired frequency response.

The flaccid membrane which forms a wall or portion of the membrane-walled chamber 30, 48 is preferably formed of one or more polymeric materials in a thin film form which exhibit the desired pliability, with minimal gas or liquid permeability so as to minimize outward migration of gas from the catheter 12 and/or inward migration of water vapor or other matter from any body fluid coming into contact with the outer surface of the membrane 24, 40. Examples of polymeric materials which may be utilized alone, or in combination, for formation of the membrane 24, 40 include polyurethane, polyvinyl cloride (PVC) and polyvinylidene (e.g., Saran).

In applications wherein the catheter 12 is intended to remain inserted into the mammalian body for an extended period of time (e.g., six (6) hours) water vapor may migrate from the surrounding body fluid, into the gas-filled membrane-walled chamber 30, 48 of the catheter 12. Such water vapor may condense in the exteriorized proximal portion of the catheter 12 if such exteriorized proximal portion of the catheter 12 is at a lower temperature than the intracorporeally inserted distal portion thereof. Such condensation of liquid within the gas-filled pressure monitoring lumen 22 may interfere with the desired communication of pressure changes through the lumen 22. Initially, the inertial effects of moisture accumulating within the pressure-monitoring lumen 22 may affect the frequency response of the system. As the amount of moisture within the pressure monitoring lumen 22 increases, such moisture may become large enough in quantity to introduce a offset error into the system. Thus, in catheters 12 of the present invention intended for long term indwelling use, it is desirable to incorporate or provide a moisture-removing material or apparatus to prevent the formation and/or accumulation of condensation moisture within the pressure monitoring lumen 22.

In particular, a hygroscopic material may be disposed within the gas-filled pressure monitoring lumen 22, or coated on the inner walls thereof as indicated at 23 in FIG. 1A, to take up and hold any moisture which forms in the lumen 22 during use of the catheter 12 Polyacrylamide is a suitable hygroscopic material for this purpose. Polyacrylamide beads may be adhered to the luminal surface of the pressure monitoring lumen 22 by way of an adhesive. Alternatively, a polyacrylamide coating may be formed on the lumenal surface of the gas-filled pressure monitoring lumen 22.

Alternative materials and/or methods for preventing the formation of, or removing, condensation moisture from the pressure monitoring lumen 22 include a wicking thread or capillary member disposed within the lumen. Alternatively, an electrical resistance heater or other heating element may be formed within or applied to the exteriorized proximal portion of the catheter body so as to maintain such exteriorized portion of the catheter 12 at the same temperature as the intracorporeally inserted distal portion thereof. Such warming of the proximal portion of the catheter body will avoid the temperature differential between the intracorporeally inserted and exteriorized portions of the catheter and may avoid the formation of condensation moisture within the proximal portion of the catheter body.

The membranous wall of the gas-filled membrane-walled pressure monitoring chamber 30, 48 may be formed of any suitable material flexible enough to give accurate pressure readings through the catheter 12. One presently preferred material is polyurethane film. Other polymeric film materials may also be usable. The propensity for outward migration of gas from the gas-filled chamber 30, 48, and the corresponding propensity for inward migration of water vapor from the surrounding body fluids, will depend on the permeability of the material of which the membranous wall of the membrane-walled chamber 30, 48 is formed.

ii. Catheter Embodiments Having Gas-Filled Membrane-Walled Pressure Sending Chamber On Distal Tip Of Catheter As shown in FIG. 1, a basic pressure monitoring catheter system 10 of the present invention comprises an elongate flexible air column catheter 12 which is connectable to a pressure sensor apparatus 14. A cable 16 connects the pressure sensor apparatus 14 to a monitor 18 on which an indication of the sensed pressure is displayed, In the basic embodiment of FIG. 1, the catheter 12 of the system 10 comprises an elongate pliable catheter body 20 having an outer surface 36 and a hollow lumen 22 extending longitudinally therethrough.

The catheter lumen 22 has an inner diameter $D_1$. The outer surface 36 of the catheter body 20 has an outer diameter $D_2$.

A bulbous pressure sensing membrane 24 is mounted on the distal end of the catheter body 20. The bulbous membrane 24 is preferably formed of a polymeric film such as polyurethane, polyvinyl chloride (PVC), and/or polyvinylidene (Saran) and has a preferred thickness of approximately 0.5–1.5 mm.

The bulbous membrane 24 on the distal end of the catheter body 20 has an outer surface 26 and an inner surface 28. The inner surface 28 of the bulbous membrane 24 defines the distal boundary or wall of a gas-filled chamber 30 adjacent the distal end of the catheter body 20. The distal gas-filled membrane-walled chamber 30 is in fluidic communication with the catheter lumen 22. The bulbous membrane 24 will flex or move in response to changes in pressure against the outer surface 26 of the membrane 24. Such flexing or movement of the distal membrane 24 will result in corresponding compression or decompression of the gas within distal chamber 30 and lumen 22 of the catheter 12, thereby communicating such changes in pressure to the pressure sensor 14 and monitor 18.

As shown in FIGS. 1a–1c, the bulbous distal membrane 24 and gas-filled membrane-walled distal chamber 30 may be manufactured in various different ways, with various different configurational attributes. For example, in the basic embodiment shown in FIG. 1a, a small region at the distal end of the catheter body 20 is turned down or cut in so as to provide a reduced-diameter shoulder upon which the membrane 24 may be affixed.

The bulbous distal membrane 24 may be preferably sized and configured such that, when in its distended operative configuration, the outer diameter of the bulbous membrane 24 is substantially the same as, or only slightly larger than, the adjacent outer diameter $D_2$ of the distal end of the catheter body 20. Also, the bulbous distal membrane 24, when in its distended operative configuration, will preferably extend distally beyond the distal end of the catheter body 12 by a distance no more than eight (8) times the diameter of the distal end of the catheter body 12.

In the alternative embodiment shown in FIG. 1b, the volume of the gas-filled distal chamber 30 may be enhanced by forming a hollow region 32 within the distal end of the catheter body 20 such that the internal volume of the chamber 30 will be made up of the volume of space defined by the inner surface 28a of the diaphragm 24a in combination with the volume of the hollow region 32 within the distal end of the catheter body 20.

In another alternative configuration shown in FIG. 1c, a bellows type membrane cap 24b is affixed to the distal end of the catheter body 20. Such bellows-type membrane cap 24b has a series of pleats of folds 34 which will flex back and forth in response to changes in pressure on the outer surface thereof.

In the basic pressure monitoring catheter embodiment shown in FIGS. 1–1d, any changes in the pressure exerted against the outer surface 26 of the bulbous distal membrane 24 will cause the bulbous distal membrane 24 to flex or translate inwardly, thereby compressing the gas contained within the distal chamber 30 and lumen 22 of the catheter.

A proximal connector 38 on the proximal end of the catheter lumen 22 is coupleable to a pressure sensor 14 to enable the pressure sensor 14 to receive and sense changes in pressure within the catheter lumen 22. In one preferred embodiment, the proximal connector 38 has an inner bore 39 which is substantially the same size as the gas-filled lumen of the catheter so as not to create an expansion chamber which would adversely affect frequency response. Insertion of the proximal connector 38 into the bore of the sensor 14 to a stopping point therein entraps a defined volume of the gaseous medium within the lumen 22 and distal chamber 30 of the catheter 12. It is preferred that the proximal connector 38 and corresponding bore of the sensor 14 be specifically sized and configured such that the act of inserting the proximal connector 38 into the sensor 14 to its intended stopping point will entrap the desired volume of gas within the lumen 22 and distal chamber 30 of the catheter 12. Such preferred volume of gaseous medium within the catheter 12 will cause the distal membrane 24 to approach its fully distended configuration when the outer surface 26 of the distal membrane 24 is surrounded by ambient room air pressure. On the other end, if the catheter 12 is inserted into an anatomical position where greater than ambient pressures surround the outer surface 26 of the distal membrane 24, the distal membrane 24 will assume a less than a fully distended configuration wherefrom it will be capable of translating both inwardly and outwardly in response to respective increases and decreases in pressure in the surrounding anatomical passageway or cavity of the mammalian body.

Figure 8:
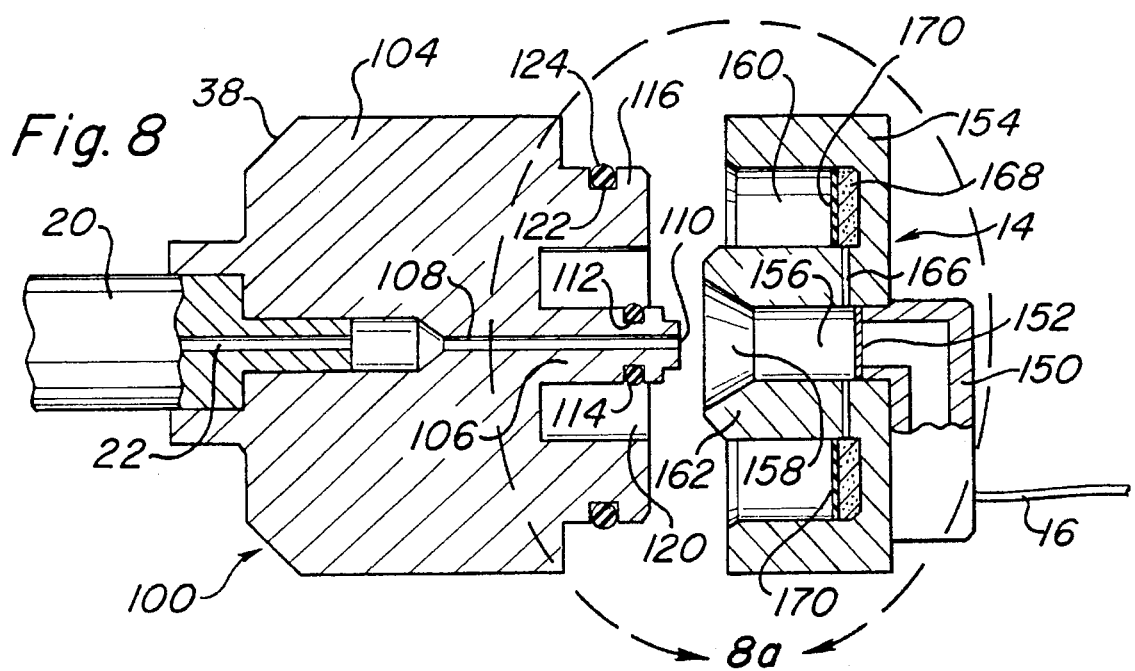
FIG. 8 is an exploded, partially sectional view of two (2) separate components which comprise a preferred pressure maintenance/pressure sensor coupling system for a) coupling the gas-filled lumen(s) of the catheter to an extracorporeally located pressure sensor and b) maintaining a desired gas pressure within the catheter lumen(s) and membrane-walled pressure monitoring chamber(s) for an extended period of time despite any diffusive loss of gas therefrom.

Additionally, in applications wherein gas is expected to diffuse out of the gas-filled distal chamber 30 and/or lumen 22 of the catheter 12, it may be desirable to utilize a more complex pressure-maintaining sensor coupling system such as that shown in FIG. 8 of this patent application, and described in more detail in subsection vii herebelow.

iii. Catheter Embodiments Having Gas-Filled Membrane-Walled Pressure Sensing Chambers On The Catheter Side Wall As an alternative to, or in combination with, the above-described embodiment wherein a bulbous gas-filled membrane-walled pressure sensing chamber 30 is positioned on the distal end of the catheter body 20, the gas column pressure monitoring catheter 10 may be configured such that the hollow gas filled lumen 22 of the catheter 12 extends through the catheter body and terminates in an aperture 43 located on the side wall of the catheter body, some distance proximal to the distal end thereof. The membrane 40 defines the outer wall of a gas-filled chamber 48 in fluidic communication with the lumen 22 of the catheter through aperture 43. By such arrangement, pressure exerted against the outer surface 42 of the membrane 40 will cause the membrane 40 to compress or move inwardly, thereby compressing the gas contained within the chamber 48 and lumen 22. Subsequent decrease in the pressure against the outer surface 42 of the membrane 40 will allow the membrane to decompress or move outwardly, thereby decreasing the pressure of gas within the chamber 48 and lumen 22. Thus, the gas-filled membrane-walled pressure monitoring chamber 48 located on the side wall of the catheter body serves to communicate changes in pressure to the externally located pressure sensor 14 in the same general manner as that described hereabove for the bulbous distal tip gas-filled membrane walled pressure sensing chamber 30.

Examples of embodiments of the catheter 12 which incorporate a gas-filled membrane-walled side wall pressure sensing chamber 48 include those shown in FIGS. 2, 2a, 3c, 4–4f, 5–5a and 7a–7b.

FIGS. 2–2b show an alternative embodiment of a catheter system 10a of the invention, wherein the catheter 12a comprises a dual lumen catheter 12b having two separate gas-filled membrane-walled pressure sensing chambers 30, 40, located on the distal tip and sidewall of the catheter 12, respectively, for simultaneous and/or separate monitoring of pressures at such separate locations on the catheter body. The catheter 12b incorporates a first lumen 22a extending longitudinally through the catheter body to an air filled distal chamber 30 having a bulbous distal tip membrane 24 of the type and construction described and shown hereabove in FIGS. 1–1c. In addition, a second lumen 22b extends longitudinally through a proximal portion of the catheter body terminating in at least one aperture 43 opening through the side wall of the catheter body at a location some distance proximal to the distal end of the catheter body 28. An annular or cylindrical membrane 40 is mounted on the outer surface 36a of the catheter body 20a at the location of the sidewall aperture 43. The annular or cylindrical membrane 40 has an outer surface 42 and an inner surface 44. A second air filled chamber 48 is defined inboard of the inner surface 44 of the annular diaphragm 40, in communication with the second lumen 22b through sidewall aperture(s) 43.

In many applications, it is desirable that the outer diameter of the annular membrane 40, when fully gas-filled and distended, not protrude more than 5 mm, and preferably not more than about 1 mm, beyond the adjacent outer surface 36a of the catheter body 12a. As shown in FIG. 2a, this may be accomplished by forming a reduced diameter region 36c of the catheter body 20a beneath the annular diaphragm 40, thereby increasing the gas containment volume of the annular chamber 48, without requiring that the annular diaphragm 40b laterally distended. Proximal and distal reduced diameter steps or shoulders 36b may be formed at either end of the reduced diameter region 36c to receive the proximal and distal ends of the cylindrical membrane 40 and to facilitate affixation or bonding of the end, of the cylindrical membrane 40 to the outer surface of the catheter body without abrupt or excessive protrusion of the membrane ends outwardly from the outer surface 36b of the catheter 12. As shown in FIG. 2a, the proximal and distal shoulders 36b may be of a depth equivalent to the thickness of the diaphragm 40, thereby causing in the outer surface 42 of the diaphragm 40 to be substantially flush and continuous with the adjacent outer surface of 36a of the catheter body 12a.

As shown in the example of FIG. 2, any catheter which incorporate two or more gas-filled pressure sensing lumens 22 may incorporate separate pressure sensor coupling components to connect the separate pressure sensors 14. In the embodiment of FIG. 2, the proximal portion of the catheter 12b is bifurcated or divided such that the first lumen 22a leads to a first proximal connector 38a and the second lumen 22b leads to a second proximal connector 38b. The first proximal connector 38a is insertable into a first pressure sensor 14a, while the second proximal connector 38b is insertable into a second pressure sensor 14b. The first pressure sensor 14a is connected to a first input jack on monitor 18 by way of first cable 16a, while the second pressure sensor 14b is connected to a second input jack on monitor 18 by way of second cable 16b. By this arrangement, the second embodiment of the system 10b shown in FIGS. 2–2b is usable to simultaneously monitor a first pressure at the distal end of the catheter and a second pressure at the second pressure monitoring location, some spaced proximal distance from the distal end of the catheter.

iv. Catheter Embodiments Designed For Specific Pressure Pressure Monitoring Applications a. Gas Column Catheters With Separate Infusion/Aspiration Lumen(s)

FIGS. 3–3d show alternative configurations of a third embodiment of a system 10c of the present invention comprising a gas column pressure monitoring catheter incorporating one or more working lumens 50 for fluid infusion/withdrawal. The incorporation of such separate working lumen(s) 50 may be particularly useful in pressure monitoring applications wherein it is desirable to withdraw samples of body fluids (e.g., blood, cerebrospinal fluid, etc . . . ) or infuse fluids/drugs through the catheter 12. The configuration of the catheter 12c shown in FIGS. 3–3b incorporates an air-filled lumen 22 and bulbous distal membrane 24 of the type described hereabove and shown in FIGS. 1–1c, and further incorporates at least one working lumen 50 which extends longitudinally through the catheter 12c and opens through at least one fluid infusion/aspiration aperture 52 formed in the catheter 12c. The proximal portion of the catheter 12c is bifurcated such that the air-filled pressure monitoring lumen 22 extends through a first bifurcation having a first connector 38 coupleable to a pressure sensing apparatus 14 and monitor 18 as described hereabove. The working lumen(s) 50 extends through a second furcation of the proximal catheter 12c to a connector 54 having a configuration suitable for connection to any desired fluid infusion/aspiration apparatus or system. In the embodiment shown, a two way stopcock 56 is connected to connector 54 and a syringe 58 is mounted to the stopcock 56 for infusion of fluid through or aspiration of fluid from working lumen(s) 50.

The alternative configuration shown in FIGS. 3c–3d comprises an elongate flexible catheter body 20 having a gas-filled pressure sensing lumen 22 extending longitudinally therethrough and terminating in an aperture 43 formed in an annular depression cut into the side wall of the catheter body 20. An annular membrane 44 is mounted about the outer surface of the catheter body 20, in the manner described hereabove with respect to the embodiment shown in FIG. 2a. By such arrangement, an air-filled membrane-walled pressure monitoring chamber 48 is formed about the outer surface of the catheter body, bounded in part by the inner surface 44 of the cylindrical membrane 40. The gas-filled lumen 22 is coupleable by way of connector 38 to a pressure sensing apparatus 14 and monitor 18, as described hereabove, so as to monitor changes in pressure against the outer surface 42 of the membrane 40. A first working lumen 50a and a second working lumen 50b extend longitudinally through the catheter body 20. The first working lumen 58 terminates in an inlet/outlet aperture 52a formed in the sidewall of the catheter body 20, proximal to the pressure monitoring membrane 40. The second working lumen 50b extends longitudinally through the catheter body and terminates in an inlet/outlet aperture 52b formed in the distal end of the catheter body. By such arrangement, fluids may be separately infused through working lumens 50a, 50b and blood samples may be separately withdrawn through working lumens 50a, 50b, without interruption of the pressure monitoring function of the membrane-walled gas-filled chamber 48 and associated gas-filled lumen 22.

The embodiments of the catheter shown in FIGS. 3–3d are particularly suitable for monitoring of arterial and or central venous pressures in that they provide for the withdrawal of periodic blood samples, and/or the infusion of fluids or drugs through the catheter 12c without interruption of its pressure monitoring function.

b. Pulmonary Artery Catheters

Figure 5:
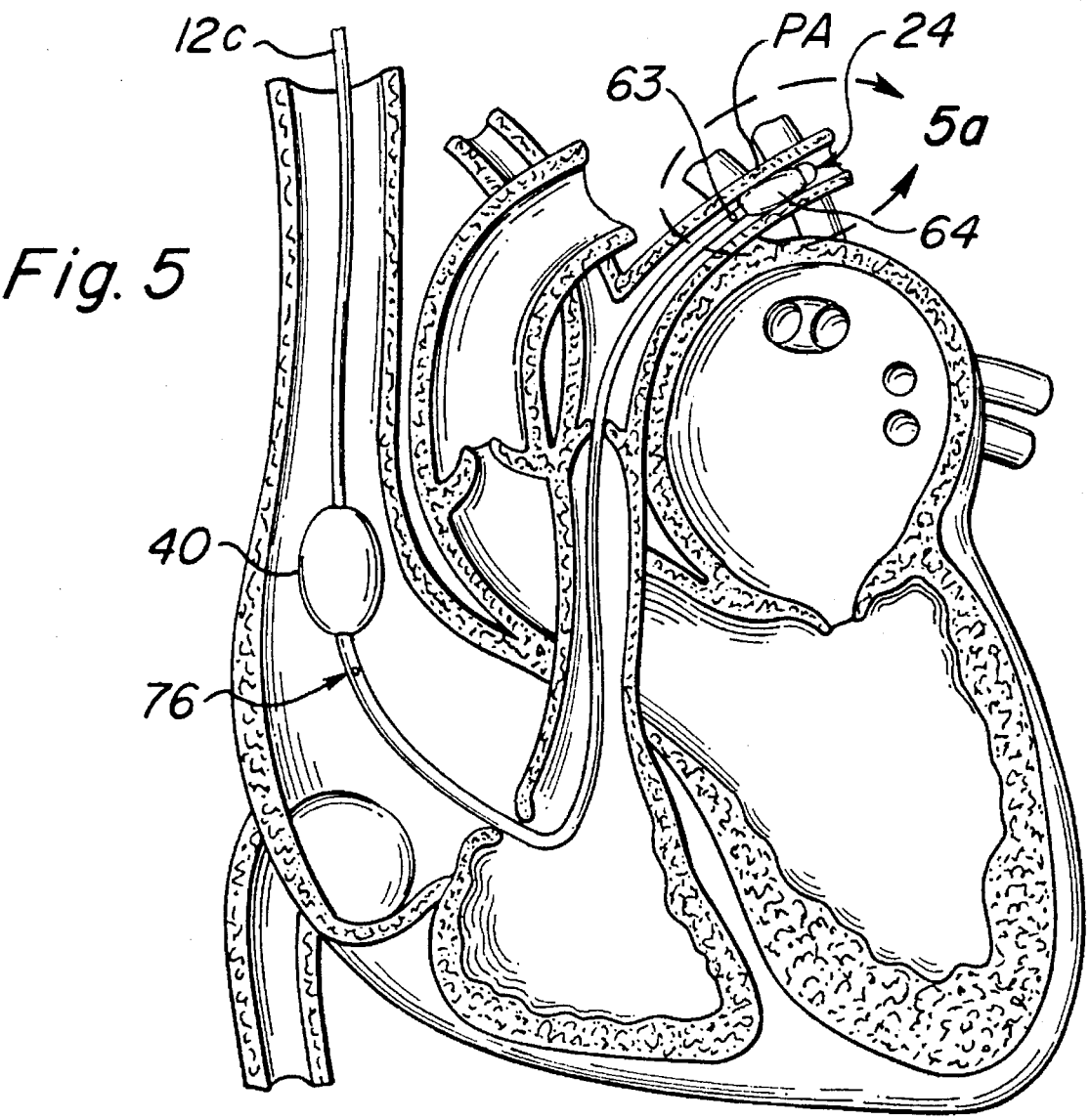
FIG. 5 is a partial cut-away perspective view of a human heart and thoracic blood vessels having the pulmonary artery catheter of FIG. 4 operatively positioned therein.
Figure 5A:
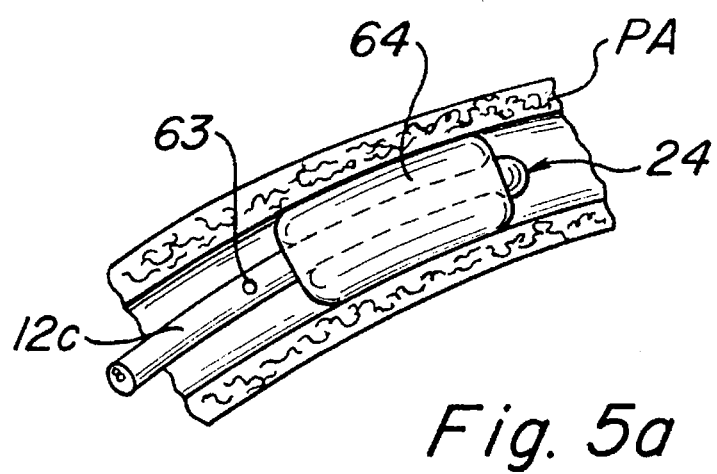
FIG. 5a is an enlarged view of region 5a of FIG. 5.

FIGS. 4–5a shows an embodiment of the system 10c wherein the catheter 12c is specifically configured and equipped to be used in place of a prior art Swan-Ganz Right Heart Pulmonary Artery Catheter. The pulmonary artery catheter 12c of the present invention is preferably equipped for (a) monitoring pulmonary artery pressures and (b) determining cardiac output by known thermal dilution methodology. Also, as described herebelow, the pulmonary artery catheter 12c may also incorporate one or more working lumens for infusing fluids and/or withdrawing blood samples from specific locations within the cardio-pulmonary portions of the circulatory system.

As shown, the pulmonary artery catheter 12c comprises an elongate pliable catheter body 20c having a first gas-filled pressure monitoring lumen 22a, a second gas-filled pressure monitoring lumen 22b, a balloon inflation-deflation lumen 60, a pulmonary artery sample withdrawal lumen 61 and a thermistor wire 62 extending longitudinally therethrough.

The first gas-filled pressure monitoring lumen 22a extends longitudinally through the catheter body to the distal tip thereof. A bulbous distal membrane 24 is mounted on the distal end of the catheter body 20c, in the manner shown and described in relation to FIGS. 1–1a hereabove. As described above, the inner surface 28 of the bulbous distal membrane 24 defines the volume of the gas filled distal chamber 30, which is in fluidic communication with the first gas-filled pressure monitoring lumen 22a. The proximal end of the first gas-filled pressure monitoring lumen 22a extends through a first furcation on the proximal end of the catheter to a proximal connector 38a. The proximal connector 38a is connectable to a first pressure sensor 14a. Pressure sensor 14a is connectable, by way of cable 16a, to a first input jack on monitor 18.

The second gas-filled pressure monitoring lumen 22b extends longitudinally through the catheter body 20c, to a termination point some distance proximal to the distal tip of the catheter body 20c.

The second gas-filled pressure monitoring lumen 22b extends longitudinally through the catheter body 20c and terminates at a second pressure monitoring location a spaced distance proximal to the distal end of the catheter body 22a. The outer surface 36c of the catheter body 20c is modified, and an annular or cylindrical membrane 40 is mounted thereon, as shown and described hereabove in relation to FIG. 2a. In this pulmonary artery catheter 12c, the distance $L_1$ from the distal end of the catheter to the second pressure monitoring location is sized to correspond to the anatomical distance between the desired pulmonary artery position of the distal end of the catheter 12c and an acceptable pressure monitoring location within the superior vena cava SVC of the heart.

Additionally, in the pulmonary artery catheter 12c of the present invention, a pulmonary artery occlusion or "wedge" balloon 64 is mounted about the distal end of the catheter body 20c. The pulmonary artery occlusion balloon 64 is alternately inflatable and deflateable to permit periodic volitional occlusion of the pulmonary artery wherein the distal end of the catheter 12b is located, for purposes of obtaining periodic measurements of pulmonary capillary wedge pressure (PCWP). The balloon inflation/deflation lumen 60 terminates in at least one aperture 66 which opens into the interior of the pulmonary artery occlusion balloon 64. The balloon inflation/deflation lumen 60 of the catheter 12c, extends proximally through a balloon inflation/deflation furcation or branch 68 of the catheter 12c and terminates in a Leur connector or similar arrangement whereby a stopcock 70 and syringe 72 may be attached for purposes of periodically inflating/deflating the pulmonary occlusion balloon 64.

A thermistor 70 is mounted within the catheter 12c near the distal tip thereof, and is connected to the distal end of the thermistor wire 62. The proximal end of the thermistor wire 62 extends out of the proximal portion of the catheter 12c and is connectable to a cardiac output computer 72 for measurement of cardiac output by known thermal dilution methodology. An optional thermal dilution injectate infusion lumen (not shown) extends through a proximal portion of the catheter body 20c, terminating in an injectate infusion aperture 76 located a spaced distance L2 from the distal end of the catheter.

The injectate infusion lumen 74 extends proximally through an infusion furcation or branch 78 and terminates in a Leur connector or other arrangement whereby a stopcock 80 and or syringe 82 may be utilized to infuse the desired thermal dilution injectate through the injectate lumen 74 and out of injectate aperture 76.

When it is desirable to withdraw a sample of mixed venous blood from the pulmonary artery, stop cock 83 may be opened and syringe 85 may be utilized to draw blood through aperture 63, and proximally through withdrawal lumen 61 such that the desired blood sample may be obtained. Thereafter, heparinized saline or other acceptable fluid may be instilled into lumen 61 and flushed therethrough so as to maintain patency of the sample withdrawal lumen 61 and to avoid undesirable back up of blood thereinto.

The desired operative positioning, and methods of use, of the pulmonary artery catheter system 10c is shown in FIGS. 5–5a. The cardiac anatomical structures and blood vessels shown in FIG. 5 are labeled in accordance with the following legend:

PV . . . Pulmonary Veins
PA . . . Pulmonary Artery
RPA . . . Right Pulmonary Artery
LPA . . . Left Pulmonary Artery
SVC . . . Superior Vena Cava
IVC . . . Inferior Vena Cava
A . . . Aorta RA ... Right Atrium
RV ... Right Ventricle
LA ... Left Atrium
LV ... Left Ventricle
AV ... Aortic Valve
MV ... Mitral Valve
PuV ... Pulmonary Valve With reference to FIG. 5, the pulmonary artery catheter 12c may be percutaneously inserted into a peripheral vein, such as the external jugular, internal jugular, subclavian, femoral or antecubital vein and advanced into the superior vena cava SVC. At that point, the first and second connectors 38a, 38b are connected to the corresponding pressure sensors 14a, 14b to permit monitoring of the pressures sensed by the bulbous distal diaphragm 24 and annular diaphragm 40 during insertion of the catheter. The pulmonary occlusion balloon 64 is then inflated by opening stopcock 70 and injecting a small amount of inflation fluid (e.g., air or $CO_2$) by syringe 72, through inflation/deflation furcation 68, through inflation/deflation lumen 60 and into the pulmonary occlusion balloon 64. In most embodiments approximately 1.0-1.5 mls. of inflation fluid will be sufficient for this purpose. The catheter is then advanced through the right ventricle RV, through the pulmonary valve PuV and into a branch of the pulmonary artery PA, until a typical pulmonary capillary wedge pressure (PCWP) tracing is observed on monitor 18. This will indicate that the catheter 12c has reached its desired operative position wherein the distal tip of the catheter 12 is positioned in the pulmonary artery PA. Proper positioning of the catheter 12c may also be confirmed by radiographic means.

One reason for inflating the pulmonary artery occlusion balloon 64 during advancement through the right ventricle is to cushion the distal tip of the catheter 12c so as to avoid the inducement of arrhythmias due to bumping of the hard catheter tip against the walls of the right ventricle. As shown in FIG. 4a, the inflated pulmonary artery occlusion balloon 64 is shapped and positioned such that it serves to fully cushion the entire distal end of the catheter body 20c, thereby furthering the goal of preventing the hard catheter body 20c from contacting or bumping against the walls of the ventricle as the catheter 12c is advanced therethrough.

with the catheter 12c in its desired operative position, as shown in FIG. 5, and the pulmonary occlusion balloon 64 deflated, the tracings on monitor 18 will provide continual monitoring of pressures in a) the pulmonary artery via the bulbous distal membrane 24 and b) the superior vena cava SVC via the annular proximal membrane 40.

Periodic determination of the pulmonary artery wedge pressure (PAWP) is achieved by inflating the pulmonary artery occlusion balloon 64 as described hereabove. Such inflation of balloon 64 will cause the monitor tracing relating to the pressure against the outer surface of the bulbous distal membrane 24 to indicate the present pulmonary artery wedge pressure (PAWP). After the desired pulmonary artery wedge pressure (PAWP) reading has been obtained, the balloon 64 will be deflated and the catheter will be allowed to continue its ongoing pressure monitoring functions as described hereabove.

When it is desired to measure cardiac output, the cardiac output computer 72 will be actuated, and prepared for use. Stopcock 80 will be open and syringe 82 will be utilized to inject a desired quantity of room temperature or chilled injectate (e.g., 0.9 percent saline solution) through the injectate furcation 78, through injectate lumen 74 and out of injectate aperture 76. The bolus of thermal dilution injectate will thus inter the right atrium RA and be carried by the cardiac circulation into the pulmonary artery PA whereat the distal end of the catheter 12c is positioned. The momentary decrease in temperature resulting from such cardiac pumping of the injectate bolus into the pulmonary artery PA will be sensed by the thermistor 70 and will be transmitted to the cardiac output computer 72. The cardiac output computer 72 is programmed and adapted to provide a computed cardiac output value based on the rate of temperature change sensed at the thermistor 70 following injection of the injectate bolus. Typically, multiple cardiac output determinations are made by the average of such multiple determinations is taken as the current cardiac output of the patient.

c. Intracranial Pressure Monitoring Catheters

Another alternative embodiment of the system 10d of the present invention, is shown in FIGS. 6–6d, is adapted for monitoring of intracranial pressures.

With reference to FIGS. 6–6d, there is provided a catheter 12d which incorporates all of the elements of the catheter shown in FIG. 3, with an additional blind stylet-receiving lumen or cul-de-sac 70 which extends from a stylet entry aperture 72 formed in the sidewall of the catheter body 20d, to a blind distal end 74 near the distal tip of the catheter body 20d. By such arrangement, a stiffening wire or stylet 76 may be inserted through the stylet entry aperture 74, and advanced into the blind stylet lumen or cul-de-sac 70 to a point where the distal end of the stylet 76 abuts against the blind distal end 74 of the stylet lumen or cul-de-sac 70. Thus, when inserted in this manner, the stiffening stylet 76 will lend rigidity to only a distal portion of the catheter 12b, as shown.

The provision of the blind stylet lumen 70 and stylet entry aperture 72 of the catheter 12d, allows the catheter to be inserted by way of a scalp tunnel technique whereby a subcutaneous tunnel ST is formed in the scalp of the patient and a skull bore hole B is formed at one end of the subcutaneous tunnel ST. The catheter 12d is passed, distal end first, through the scalp tunnel, and the distal portion of the catheter is exteriorized from the end of the tunnel adjacent the bore hole BH. The stiffening stylet 76 is then inserted into the stylet entry aperture 72 and advanced into the blind stylet lumen or cul-de-sac 70 until the distal end of the stylet meets the distal end of 74 of the blind lumen or cul-de-sac 70. Thereafter, the distal portion of the catheter is inserted through the skull bore hole B, and advanced downwardly through the brain so as to enter the desired ventricle V of the brain. The stylet 76 is then extracted and removed, the catheter 12d is pulled taut and the end of the subcutaneous tunnel adjacent the bore hole B is closed by way of sutures or other appropriate means.

With the catheter 12b operatively positioned in the ventricle V of the brain, as shown in FIG. 6d, fluctuations or changes in the pressure of the cerebrospinal fluid contained within the ventricle V will register against the outer surface 26 of the bulbous distal membrane 24 and will be transmitted through the air filled distal chamber 30 and lumen 22 of the catheter 12b. Such changes in pressure will then be received and converted to electrical signals by pressure sensor 14. Electrical signals from sensor 14 will pass through cable 16 and will be displayed or recorded by intracranial pressure monitor 18d.

The fluid infusion/aspiration lumen 50 of the catheter 12d may be utilized to withdraw periodic small samples of cerebral spinal fluid for laboratory analysis and/or for controlled venting of excess cerebrospinal fluid so as to avoid excessive pressure build-up within the cranium.

In some cases it may be desirable to operatively position the pressure monitoring membrane-walled chamber of the intracranial pressure monitoring catheter within the parenchyma of the brain, rather than in the ventricle V thereof. In such embodiments, it may be desirable to utilize a side wall mounted membrane-walled pressure monitoring chamber, in communication with the gas-filled lumen 22 of the catheter 12b. Such side wall mounted membrane-walled chamber may be in the configuration of the side-wall chamber 48 shown in FIG. 2. In such embodiments, it may be desirable to also provide a working lumen which extends through the distal tip of the catheter such that, while the side wall membrane walled chamber 48 is located at a parenchymal location, the distal end opening of the working lumen of the catheter may extend into the ventricle to provide access for purposes of withdrawing samples of cerebrospinal fluid, or venting cerebrospinal fluid to avoid excessive intra cranial pressurization.

d. Intrauterine Pressure Monitoring Catheters

Figure 7B:
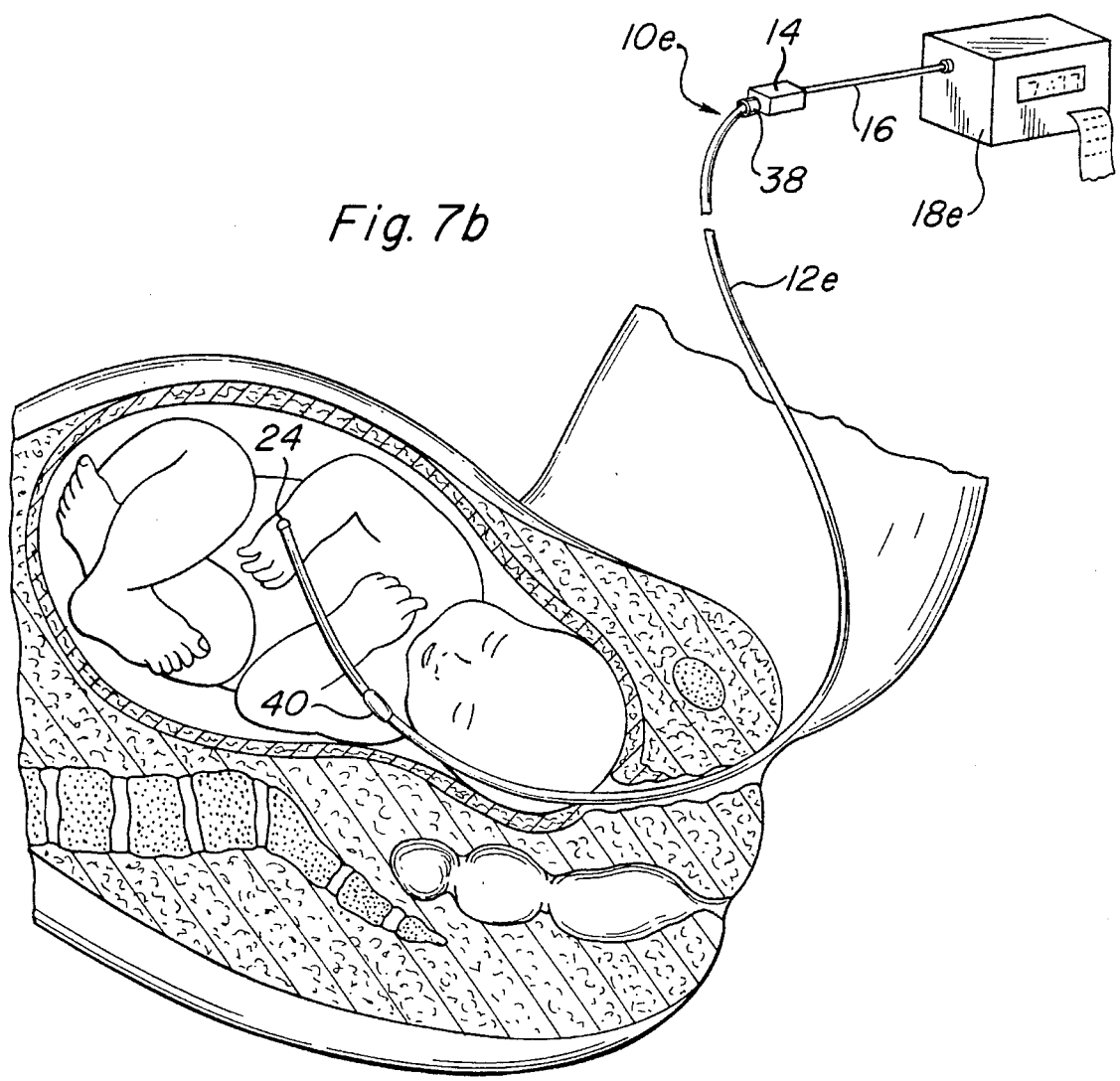
FIGS. 7a and 7b are perspective view of a sixth embodiment of a gas-filled pressure monitor catheter system of the present invention intended for monitoring of intrauterine pressures.
Figure 7A:
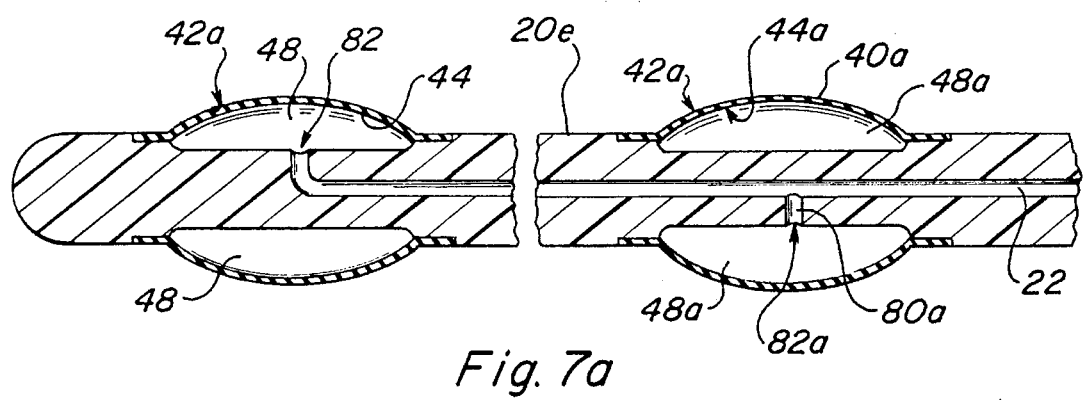

Another alternative embodiment of the system 10e, as shown in FIGS. 7–7a, is adapted for obstetrical monitoring of intrauterine pressures.

The intrauterine pressure monitoring catheter 12e comprises an elongate pliable catheter body 20e having a one or two annular sidewall diaphragm 48a, 48b, as described hereabove in relation to the embodiment shown in FIGS. 2–2b. However, in the catheter 12e shown in FIGS. 7 and 7a, a single air-filled pressure monitoring lumen 22 extends longitudinally through the catheter body 20e and commonly opens into a sidewall gas-filled membrane-walled pressure sensing chamber 48a, 48b and a proximal gas-filled membrane-walled pressure sensing chamber 48 (through lateral passageway 80 and aperture 82). By this arrangement, the air filled lumen 22 receives pressure input from both pressure sensing chambers 30 and 48 and terminates proximally in a single connector 38. The single proximal connector 38 is insertable into pressure sensor 14 such that changes in air pressure within lumen 22 are sensed by pressure sensor 14 and transmitted to intrauterine pressure monitor 18e by way of cable 16.

AS illustrated in FIG. 7b, the catheter 12e is inserted transvaginally into the gravid uterus and positioned such that one or both of the gas-filled membrane-walled pressure sensing chambers 48a, 48b are located within a suitable pressure monitoring environment such as in a region filled with amniotic fluid. If, however, during labor or delivery, the amniotic fluid shifts or moves within the uterus, resulting in one of the gas-filled membrane-walled chambers 48a or 48b becoming unresponsive to changes in intrauterine pressure, the remaining chamber 48a or 48b will continue to provide accurate indications of changes in intrauterine pressure. Thus, once the catheter 12e has been operatively positioned within the gravid uterus, it will be unnecessary to shift or move the position of the catheter in the event that only one of the pressure sensing membranes 48a, 48b remains responsive to changes in intrauterine pressure.

Although the embodiment shown in FIGS. 7–7a employs a single gas-filled lumen 22, it will be appreciated that separate gas-filled lumens may be provided to permit separate simultaneous monitoring of the pressures received by membrane-walled chambers 48a and 48b. In embodiments which incorporate two separate lumens 22, leading separately to the membrane-walled chambers 48a and 48b, an additional proximal furcation and coupling apparatus 12 (shown in phantom lines on FIG. 7) may be provided to permit connection of the catheter 12e to a dual-channel intrauterine pressure monitor. The monitor may then be utilized to simultaneously monitor pressures at both membrane-walled chambers 48a and 48b, or may be switched back and forth to alternately monitor pressure sensed by chamber 48a and 48b. This modified embodiment of the catheter 12e shown in FIGS. 7–7a will be particularly useful in clinical applications wherein it is desired to simultaneously or separately monitor contractions within separate regions of the uterus for purposes of ascertaining whether clinically normal or abnormal labor is occurring.

Also, although the embodiment shown in FIGS. 7–7a employs two (2) side wall gas-filled chambers, it will be appreciated that one of the gas filled chambers may be alternatively positioned on the distal end of the catheter, as shown in FIG. 1.

Additionally, the intrauterine catheter 12e may incorporate one or more working lumens 2 (not shown) terminating in one or more inflow/outflow apertures (not shown) so as to permit infusion of fluids into the uterus and/or withdrawal of amniotic fluid samples therefrom.

iv. A Preferred Diffusive Make-Up Gas System For Maintaining A Desired Volume Of Gas In The Catheter It will be appreciated that, depending on the material of which the pressure sensing membrane 24, 40 is formed, and the corresponding total partial pressure of gases dissolved in the surrounding fluid, the gas contained in the gas-filled chamber 30, 48 may diffuse outwardly through the pressure sensing membrane 24, 40 so as to result in depletion of the gas pressure within the gas-filled chamber(s) 30, 48 and/or lumen(s) 22 of the catheter 12. For example, in applications wherein the catheter 12 is inserted into the venae cava or right atrium for purposes of monitoring central venous pressure, the total partial pressures in the surrounding venous blood in a patient breathing room air will typically total no more than the approximately 700 mm/Hg. Because the partial pressure of gasses in the room air totals approximately 760 mm/Hg, there will be continual outward diffusion of gas through the pressure sensing membrane 24, 40 of the catheter 12. If such outward diffusion is allowed to continue over an extended period of time, the remaining quantity of gas in the gas-filled pressure monitor and column of the catheter 12 will fall below acceptable levels, thereby resulting in an inability to obtain the desired pressure reading or tracing.

Figure 8A:
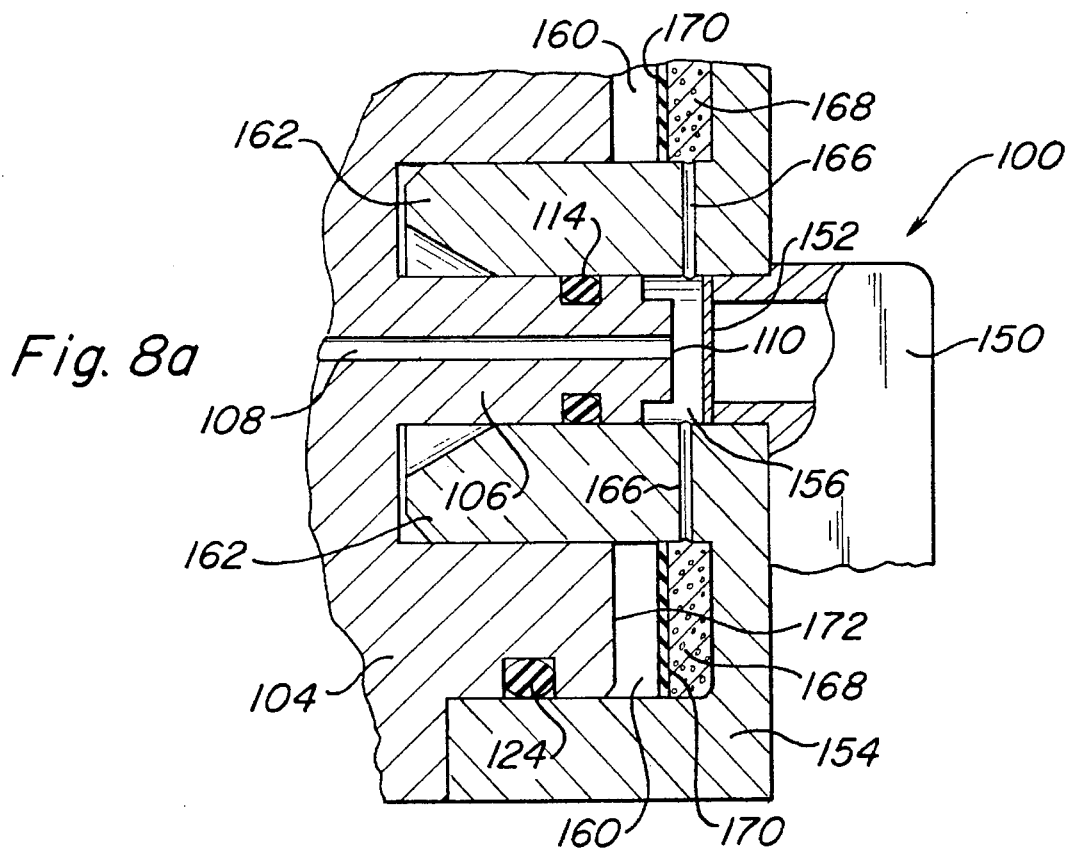
FIG. 8a is a non-exploded view of the components of FIG. 8, operatively coupled to one another.

In view of the above-stated problem of outward diffusion of gas from the gas-filled column of the catheter 12, the means by which the catheter 20 is coupled to the attendant pressure sensor may incorporate a sensor coupling/catheter inflation system 100 as shown in FIGS. 8–8a.

The presently preferred sensor coupling catheter inflation system 100 is incorporated into the proximal connector component 38 positioned on the proximal end of the catheter body 20, and in the corresponding pressure sensor component 14 which operates to sense and quantify the changes in gas pressure within the gas-filled pressure monitoring lumen 22 of the catheter 12.

As shown in FIG. 8, the proximal connector component 38 may be in the configuration of a male connector and the pressure sensor component 14 may be correspondingly configured as a female connector so that the proximal connector component 38 of the catheter 12 may be inserted into and frictionally held within the corresponding portion of the pressure sensor component 14.

In the embodiment shown, the proximal connector component 38 comprises a rigid or solid body 104 of generally round configuration having a generally cylindrical male portion 106 extending in the proximal direction from the center of the rigid body 104. A hollow gas-filled bore 108 extends longitudinally through the central male portion 106, and through the rigid body 104 of the proximal connector component 38, in fluidic communication with the proximal end of the lumen 22 of the catheter body 20. Hollow bore 108 terminates in a proximal aperture 110 at the proximal end of the central male portion 106. An annular O-ring seating groove 112 is formed about the outer surface of the central male portion 106 and a first O-ring 114 is seated therewithin.

A generally annular second male portion 116 surrounds the central male portion 106, with an annular groove or depression 120 existing therebetween. An outer 0-ring seating groove 122 is formed about the outer surface of the outer male portion 116 and a second O-ring 124 is seated therewithin.

The pressure sensor component 14 comprises a pressure sensing apparatus 150 having a pressure receiving surface 152 formed thereon to receive and sense changes in adjacent air pressure. Numerous commercially available pressure sensors may be utilized, including those which incorporate the sensing apparatus commercially available as part No. MPX 2300D from Motorola Corporation, Phoenix, Ariz.

In addition to the pressure sensing apparatus 150, the pressure sensor component 14 further comprises a rigid female coupler body 154 having a generally cylindrical central receiving well 156 formed therein. The central receiving well 156 has a chamfered or angularly relieved mouth portion 158 sized and configured to facilitate insertion of the corresponding central male portion 106 of the proximal connector component 38 thereinto. The cylindrical inner wall of the central well 156 has a diameter slightly less than the outer diameter of the first O-ring 114 such that when the central male portion 106 of the proximal connector component 138 is inserted into the central well 156 of the pressure sensor component 14, the first O-ring 14 disposed about the outer surface of the central male portion 106 will engage the surrounding surface of the central well 156, thereby frictionally holding the central male portion 106 within the central receiving well 156.

The pressure receiving diaphragm or port 152 of the pressure sensing apparatus 150 is positioned at the base of the central receiving well 156 such that when the central male portion 106 of the proximal connector component 138 is inserted thereinto, the pressure receiving diaphragm or port 152 of the pressure apparatus 150 will receive and sense changes in gas pressure communicated through the aperture 110 at the end of the central male portion 106.

An annular receiving well 160 is formed annularly about the central receiving well 156, and is separated from the central receiving well 156 by an annular boss 162 formed about the central receiving well 156 of the female connector body 154.

A plurality of gas passageways or small bores 166 extend from the base of the annular receiving well 160 through the cylindrical boss 162 and into the central receiving well 156, adjacent the pressure sensing diaphragm or port 152 of the pressure sensing apparatus 150. An annular gas permeable member 168 is positioned in the basal portion of the annular receiving well 160, such that gas which percolates, flows or is driven through the permeable member 168 will pass into passageways 166. Annular gas permeable member 168 may be formed of any suitable material which will permit pressurized gas to percolate, flow or be driven from the annular receiving well 160, through gas permeable member 168, through passageways 166, and into the central receiving well 156.

An annular membrane 170 is positioned on the exposed surface of the annular gas permeable member 168 such that gas contained within the annular receiving well 160 must pass through membrane 170 before flowing, percolating or being driven through gas permeable member 168. The membrane 170 may be formed of the same material, at the same thickness, as the pressure receiving membrane(s) 24, 40 which are positioned on the gas-filled pressure monitoring chamber(s) 30, 48 of the catheter 12.

The operative functions of the preferred sensor connecting/pressure maintaining system 100 may best be appreciated by viewing the showing of FIG. 8a wherein the proximal connector component 38 is operatively inserted into and coupled with the pressure sensor component 14.

With reference to FIG. 8a, it will be appreciated that the central male portion 106 is longer than the surrounding outer male portion 116 such that when the central male portion 106 is fully advanced into the central receiving well 156, the end of boss 162 will abut against the floor of the annular groove or depression 120, the aperture 110 at the end of the central male portion 106 will be immediately adjacent the port or diaphragm 152 of the pressure sensing apparatus 150, with a small unoccupied portion of the central well 156 remaining therebetween. When so inserted, the first O-ring 114 will engage the surrounding surfaces of the central receiving well 156 so as to frictionally hold the central male portion 106 within the central receiving well 156.

The annular outer male portion 116 extends into the annular receiving well 160 such that a space exists between the frontal face 172 of the annular outer male portion 162 and the membrane 170 positioned in the floor of the annular receiving well 160. The outer O-ring 124 and outer surfaces of the annular outer male portion 160 seal against the surrounding surfaces of the annular receiving well 160 so as to cause gas to be compressed between the frontal surface 172 of the annular outer male portion 116 and the membrane 170.

As gas diffuses through the pressure-sensing membranes 24 and/or 40 of the catheter 12, the gas volume within the lumen 22 of the catheter and corresponding bore 108 of the proximal connector component 38 will decrease. However, a corresponding diffusion of gas will occur over membrane 170, from the gas compressed within the space between the frontal surface 172 of the annular outer male portion 116 and the membrane 170. As gas diffuses through membrane 170, the diffused gas will percolate flow or be driven through the gas permeable member 168, through passageways 166, and into the space between the proximal extent or end of the central male portion 106 and the adjacent diaphragm or receiving port 152 of the pressure sensor apparatus 150. Such diffused gas will then enter bore 108 and flow into the lumen 102 of the catheter 12, thereby restoring the volume of gas within the catheter and the bore 108 to the desired level.

It will be appreciated that, in order to cause the rate of diffusion through membrane 170 to be equal to, or close to, the rate at which gas diffuses outwardly over pressure receiving membranes 24 and or 40 of the catheter 12, it may be desirable to form the membrane 170 of the same material as the catheter membranes 24, 40, or to selectively adjust the thickness, area and/or material of membrane 170, and/or the pressure created with the receiving well 160 beneath the frontal surface 172 of the annular outer male portion 116, so as to provide for the desired equivalency or similarity of diffusion rates.

Also, in any embodiment of the invention wherein the means by which the catheter 20 is coupled to the attendant pressure sensor component 14 incorporates a pumping mechanism for passing a desired amount of gas into the catheter 12, such system may be modified so as to cause a first prescribed volume of gas to pass into the catheter 12 upon initial coupling of the catheter 12 to the attendant pressure sensor component 14, but to subsequently cause a different second volume of gas to pass into the catheter 12 upon subsequent recouping thereof. This aspect of the invention may be important due to the pressure change which the catheter will undergo when it is inserted into the body. For example, if the coupling system 100 is utilized to initially inflate the catheter prior to insertion of the catheter into the body, it will be desirable to inflate the catheter to less than full volume inflation because the temperature increase which the distal portion of the catheter will undergo upon insertion into the body will cause the gas to expand, thereby causing the volumetric inflation of the catheter to increase. However, subsequent reinflations of the catheter while the catheter remains in dwelling, may accomplish full inflation of the catheter to its full desired volumetric inflation, without subsequent increase in the intracatheter gas volume due to any increase in temperature. Thus, any sensor coupling/ catheter inflation system 100 may be modified to accomplish such two stage inflation whereby the initial coupling of the system 100 will pass a first volume of gas into the catheter 12 and subsequent recouplings of the system 100 will pass a greater second volume of gas into the catheter 12.

Although the invention has been described herein with respect to a number of presently preferred embodiments, it will be appreciated that various alterations, deletions, changes and modifications may be made to the above-described embodiments without departing from the intended spirit and scope of the invention. Accordingly, it is intended that all such alterations, additions, modifications and changes be included within the scope of the following claims.

What is claimed is:

1. A gas-column catheter for monitoring intravascular pressure within the vein or artery of a mammalian body, said catheter comprising:

a catheter body having a proximal end, a distal end, and an outer surface and being of a size and shape to fit within the vein or artery of said mammalian body;

a gas-filled lumen extending longitudinally through at least a portion of said catheter body;

a gas-filled membrane-walled chamber at a fast location on said catheter body, said chamber being in gaseous communication with said lumen and being of a size and shape to fit within the vein or artery of said mammalian body and to monitor said intravascular pressure, said chamber being defined at least in pan by a flaccid membrane having an inner surface and an outer surface, said membrane being configured and positioned such that:

an increase in pressure against the outer surface of said membrane will cause said membrane to move inwardly, thereby increasing the pressure of gas within said chamber and said lumen;

and a decrease in pressure against the outer surface of said membrane will allow said membrane to move outwardly, thereby decreasing the pressure of gas within said chamber and said lumen;

said gas filled lumen being thereby operable to transmit, in the proximal direction, changes in intravascular pressure exerted within the vein or artery and against the outer surface of said flaccid membrane; and a catheter-inflating connector apparatus connectable to said catheter, said apparatus being constructed such that connection of said catheter thereto will automatically cause a prescribed volume of gas to be entrapped within said catheter.

2. The catheter of claim 1 wherein said gas-filled membrane-walled chamber is located on the distal end of said catheter body.

3. The catheter of claim 1 wherein said gas-filled membrane-walled chamber is located on the outer surface of said catheter body, at a location between the proximal and distal ends thereof.

4. The catheter of claim 2 wherein:

the flaccid membrane of said membrane walled chamber located on the distal end of the catheter body is a generally bulbous membrane formed of non-elastic material which, when filled in gas of sufficient pressure to provide the desired pressure monitoring function, will protrude laterally no more than approximately two millimeters beyond the adjacent outer surface of the distal end of said catheter body.

5. The catheter of claim 2 wherein said generally bulbous distal membrane, when in its fully gas-filled operative configuration, extends distally beyond the distal tip of said catheter body by a distance of no more than eight times the diameter of the distal end of said catheter body.

6. The catheter of claim 3 wherein said membrane-walled chamber comprises an annular chamber extending about the outer surface of said catheter body and wherein said membrane comprises a generally annular membrane mounted about the outer surface of said catheter body.

7. The catheter of claim 3 wherein said membrane-walled chamber located on the outer surface of said catheter body extends no more than 3 millimeters laterally outboard of said outer surface of said catheter body.

8. The catheter of claim 1 further comprising:

means for absorbing moisture which may accumulate within said gas-filled lumen.

9. The catheter of claim 1 further comprising means for preventing condensation of moisture within at least a portion of said gas-filled lumen.

10. The catheter of claim 1 wherein said gas-filled lumen is connectable to a separate pressure sensor.

11. The catheter of claim 1 further comprising a pressure sensor incorporated into said catheter, in communication with said gas-filled lumen.

12. The catheter of claim 1 wherein said flaccid membrane is formed of material selected from the group of materials consisting of:

a) polyurethane;
b) polyvinyl chloride;
c) polyvinylidene; and
d) combinations thereof.

13. The catheter of claim 1 further comprising:

an apparatus for passing make-up gas into said gas filled lumen for replenishing gas which is lost from said catheter.

14. The catheter of claim 1 further comprising:
at least one working lumen extending longitudinally through said catheter and terminating in at least one aperture formed in said catheter body, said working lumen being usable to infuse a fluid or withdraw blood through said catheter.

15. The central venous catheter of claim 14 wherein said at least one fluid infusion lumen comprises:
a first working lumen extending longitudinally through said catheter body from the proximal end thereof and opening through a first aperture formed at a first location thereon,
a second working lumen extending longitudinally through said catheter body from the proximal end thereof and opening through a second aperture at a second location thereon.

16. The catheter of claim 1 wherein said membrane-walled chamber comprises a chamber formed on the outer surface of said catheter body at a first location between the proximal and distal ends of the catheter body.

17. The catheter of claim 1 wherein said membrane-walled chamber comprises a distal tip chamber formed on the distal end of said catheter body, and wherein said flaccid membrane comprises a generally bulbous distal membrane.

18. The catheter of claim 17 in combination with a fixed volume of gas entrapped within said lumen and within said distal tip chamber, said fixed volume of gas being sufficient to enable said bulbous flaccid membrane to move inwardly and outwardly in response to changes in said central venous pressure, and further such that said membrane protrudes laterally no more than approximately 2 mm beyond the outer surface of the distal end of the catheter body.

19. The catheter of claim 16 wherein said membrane-walled chamber formed on the outer surface of said catheter body comprises an annular chamber having an annular membrane disposed around said catheter body.

20. The catheter of claim 16 in combination with a fixed volume of gas entrapped within said lumen and within said membrane-walled chamber formed on the outer surface of said catheter body, said fixed volume of gas being sufficient to enable said membrane to move inwardly and outwardly in response to changes in said central venous pressure, and further such that said membrane protrudes laterally no more than approximately 3 mm beyond the adjacent outer surface of the catheter body.

21. The catheter of claim 1 wherein said catheter body and said flaccid membrane, when filled with sufficient gas to monitor central venous pressure, will remain smaller than the cardiovascular anatomical passageways in which said catheter is positioned so as not to occlude said passageways.

22. A gas-column catheter insertable into the vein or artery of a mammalian body for monitoring intravascular pressure changes within said mammalian body, said catheter comprising:
a catheter body having a proximal end, a distal end, and an outer surface having an outer diameter and being of a size and shape to fit within the vein or artery of said mammalian body;
a gas-filled lumen extending longitudinally through said catheter body and terminating distally in an aperture at the distal end of said catheter body, said lumen being sized to contain therein a fixed volume of gas;
a first gas-filled membrane-walled chamber located on the distal end of said catheter body and in gaseous communication with said lumen through said aperture, said first membrane-wailed chamber being defined at least in pan by a bulbous membrane mounted on and extending distally from the distal end of said catheter body and being of a size and shape to fit within the vein or artery of said mammalian body and to monitor said intravascular pressure, said membrane having an outer surface and an inner surface, said membrane being flaccid and substantially non-elastic when in its fully gas-filled operative configuration, such that;
an increase in pressure against the outer surface of said membrane will compress said membrane causing a decrease in the volume of air within said chamber and a corresponding increase in the pressure of air within said lumen;
and a decrease in pressure against the outer surface of said membrane will allow said membrane to decompress, thereby causing an increase in the volume of air within said chamber and a corresponding decrease in the pressure of air within said lumen;
said gas filled lumen being thereby operable to transmit, in the proximal direction, changes in intravascular pressure exerted within the vein or artery and against the outer surface of said flaccid membrane; and a catheter-inflating connector apparatus connectable to said catheter, said apparatus being constructed such that connection of said catheter thereto will automatically cause a prescribed volume of gas to be entrapped within said catheter.

23. The catheter of claim 22 wherein:
said bulbous distal membrane is formed of material selected from the group of materials consisting of:
A. polyurethane
B. polyvinyl chloride
C. polyvinylidene, and
D. combinations thereof.

24. The catheter of claim 22 wherein said bulbous distal membrane is configured such that, when the catheter is charged with sufficient volume of gas to carry out its intended function, said bulbous membrane will not protrude laterally more than approximately 2 mm beyond the outer surface of the catheter body at the distal end thereof.

25. The catheter of claim 22 wherein:
the catheter body has an outer diameter of less than 5 mm and said generally bulbous distal membrane has an outer diameter of less than 9mm when in its fully distended configuration.

26. The catheter of claim 22 wherein said generally bulbous distal membrane, when said catheter is charged with a volume of gas sufficient for its intended function, extends distally beyond the distal tip of said catheter body by a distance of no more than eight times the diameter of the distal end of said catheter body.

27. The catheter of claim 22 further comprising:
a second gas-filled lumen extending longitudinally through said catheter body to a second location proximal to said first membrane-walled chamber on the distal end of said catheter body;
a second gas-filled membrane-walled chamber located at said second location and in gaseous communication with said second lumen, said second gas filled chamber being defined at least in part by a second flaccid membrane mounted on the outer surface of said catheter body and having an inner surface and an outer surface such that;
i. an increase in pressure against the outer surface of said second membrane will cause said second membrane to move inwardly thereby increasing the pressure of gas within said second chamber and second lumen; and ii. a decrease in pressure against the outer surface of said second membrane will cause said second membrane to move outwardly, thereby decreasing the pressure of gas within said second chamber and said second lumen;

said second lumen being communicable with a second pressure sensing apparatus operative to sense changes in pressure within said second lumen.

28. The catheter of claim 27 wherein said second gas-filled membrane-walled chamber is configured and constructed such that, when said second gas-filled lumen and said second membrane-walled chamber are charged with sufficient volume of gas for their intended pressure monitoring function, said second flaccid membrane will protrude laterally no more than approximately 3 mm beyond the adjacent side wall of the catheter body.

29. The catheter of claim 27 wherein said second membrane-walled chamber comprises an annular chamber extending about the outer surface of said catheter body and wherein said second membrane comprises a generally annular membrane mounted about the outer surface of said catheter body.

30. The catheter of claim 22 further comprising:

means for absorbing moisture from said gas-filled lumen.

31. The catheter of claim 22 further comprising means for preventing condensation of moisture within at least a portion of said gas-filled lumen.

32. The catheter of claim 22 wherein said catheter inflating connector apparatus is further configured and constructed such that:

upon initial connection of said catheter to said catheter-inflating connector apparatus will cause a first volume of gas to be contained within said catheter; and, upon subsequent disconnection and reconnection of said catheter to said pressure sensing apparatus, said coupling apparatus will cause a second volume of gas to be contained within said catheter.

33. The catheter of claim 22 further comprising:

an apparatus for passing make-up gas into said gas-filled lumen for replenishing gas which is lost from said catheter.

34. The catheter of claim 33 wherein said apparatus for passing make-up gas into said gas-filled lumen comprises:

a diffusive make-up gas system coupled to said gas-filled lumen for replenishing gas which is lost from said catheter through outward diffusion, said diffusive make up gas system comprising:

i. a gas-filled reservoir containing gas at a pressure which exceeds the pressure of gas within the catheter lumen;

ii. a gas flow pathway through which gas may flow from said reservoir into said catheter lumen; and iii. a membranous diffusion barrier disposed within said gas flow pathway such that gas flowing from said reservoir into said lumen must pass through said membranous barrier.

35. The catheter of claim 34 wherein the gas-filled reservoir of said diffusive make-up gas system further comprises:

a gas compressing apparatus for compressing gas within said reservoir.

36. The catheter of claim 34 wherein the rate of gas diffusion through the membranous diffusion barrier of the diffusive make-up gas system is matched to the diffusion characteristics of the flaccid membrane such that, at the time of connection, the rate at which make-up gas will pass into the catheter lumen is substantially the same as the rate at which gas is lost from said catheter due to diffusion through said flaccid membrane.

37. The catheter of claim 34 wherein said diffusive make-up gas system is incorporated into a coupler to which said catheter may be coupled, said coupler being further constructed such that:

the act of coupling said catheter to said coupler will automatically result in entrapment of a preselected volume of gas within said catheter.

38. The catheter of claim 34 wherein said diffusive make-up gas system is further constructed such that:

the act of coupling said catheter to said coupler will entrap and compress a quantity of gas within the gas-filled reservoir of said diffusive make up gas system.

39. A gas-column catheter for monitoring pressure within a mammalian body, said catheter comprising:

a catheter body having a proximal end, a distal end, and an outer surface; a gas-filled lumen extending longitudinally through at least a portion of said catheter body;

a gas-filled membrane-walled chamber at a fast location on said catheter body, said chamber being in gaseous communication with said lumen, said chamber being defined at least in part by a flaccid membrane having an inner surface and an outer surface, said membrane being configured and positioned such that:

an increase in pressure against the outer surface of said membrane will cause said membrane to move inwardly, thereby increasing the pressure of gas within said chamber and said lumen;

and a decrease in pressure against the outer surface of said membrane will allow said membrane to move outwardly, thereby decreasing the pressure of gas within said chamber and said lumen;

said gas filled lumen being thereby operable to transmit, in the proximal direction, changes in pressure exerted against the outer surface of said flaccid membrane; and said catheter further including means for absorbing moisture which may accumulate within said gas-filled lumen.

40. The catheter of claim 39 wherein said means for absorbing moisture comprises a moisture absorbing material disposed within said lumen.

41. The catheter of claim 40 wherein said moisture absorbing material is polyacrylamide.

42. A gas-column catheter insertable into a mammalian body for monitoring pressure changes within said mammalian body, said catheter comprising:

a catheter body having a proximal end, a distal end, and an outer surface having an outer diameter;

a gas-filled lumen extending longitudinally through said catheter body and terminating distally in an aperture at the distal end of said catheter body, said lumen being sized to contain therein a fixed volume of gas;

a fast gas-filled membrane-walled chamber located on the distal end of said catheter body and in gaseous communication with said lumen through said aperture, said fast membrane-walled chamber being defined at least in part by a bulbous membrane mounted on and extending distally from the distal end of said catheter body, said membrane having an outer surface and an inner surface, said membrane being flaccid and substantially non-elastic when in its fully gas-filled operative configuration, such that;

an increase in pressure against the outer surface of said membrane will compress said membrane causing a decrease in the volume of air within said chamber and a corresponding increase in the pressure of air within said lumen;

and a decrease in pressure against the outer surface of said membrane will allow said membrane to decompress, thereby causing an increase in the volume of air within said chamber and a corresponding decrease in the pressure of air within said lumen;

and said gas filled lumen being thereby operable to transmit, in the proximal direction, changes in pressure exerted against the outer surface of said flaccid membrane; and said catheter further including means for absorbing moisture from said gas filled lumen.

43. The catheter of claim 42 wherein said means for absorbing moisture comprises a moisture absorbing material within said lumen.

44. The catheter of claim 43 wherein said moisture absorbing material is polyacrylamide.

45. A gas-column catheter insertable into a mammalian body for monitoring pressure changes within said mammalian body, said catheter comprising:

a catheter body having a proximal end, a distal end, and an outer surface having an outer diameter;, a gas-filled lumen extending longitudinally through said catheter body and terminating distally in an aperture at the distal end of said catheter body, said lumen being sized to contain therein a fixed volume of gas;

a fast gas-filled membrane-walled chamber located on the distal end of said catheter body and in gaseous communication with said lumen through said aperture, said fast membrane-walled chamber being defined at least in pan by a bulbous membrane mounted on and extending distally from the distal end of said catheter body, said membrane having an outer surface and an inner surface, said membrane being flaccid and substantially non-elastic when in its fully gas-filled operative configuration, such that;

an increase in pressure against the outer surface of said membrane will compress said membrane causing a decrease in the volume of air within said chamber and a corresponding increase in the pressure of air within said lumen;

and a decrease in pressure against the outer surface of said membrane will allow said membrane to decompress, thereby causing an increase in the volume of air within said chamber and a corresponding decrease in the pressure of air within said lumen;

and said gas filled lumen being thereby operable to transmit, in the proximal direction, changes in pressure exerted against the outer surface of said flaccid membrane; and said catheter further including means for means for preventing condensation of moisture within at least a portion of said gas-filled lumen.

46. A gas-column catheter for monitoring pressure within a mammalian body, said catheter comprising:

a catheter body having a proximal end, a distal end, and an outer surface; a gas filled lumen extending longitudinally through at least a portion of said catheter body;

a gas-filled membrane-walled chamber at a first location on said catheter body, said chamber being in gaseous communication with said lumen, said chamber being defined at least in pan by a flaccid membrane having an inner surface and an outer surface, said membrane being configured and positioned such that:

an increase in pressure against the outer surface of said membrane will cause said membrane to move inwardly, thereby increasing the pressure of gas within said chamber and said lumen;

and a decrease in pressure against the outer surface of said membrane will allow said membrane to move outwardly, thereby decreasing the pressure of gas within said chamber and said lumen;

said gas filled lumen being thereby operable to transmit, in the proximal direction, changes in pressure exerted against the outer surface of said flaccid membrane; and said catheter further including means for means for preventing condensation of moisture within at least a portion of said gas-filled lumen.

47. A gas-colunm catheter for monitoring pressure within a mammalian body, said catheter comprising:

a catheter body having a proximal end, a distal end, and an outer surface; a gas-filled lumen extending longitudinally through at least a portion of said catheter body;

a gas-filled membrane-walled chamber at a first location on said catheter body, said chamber being in gaseous communication with said lumen, said chamber being defined at least in pan by a flaccid membrane having an inner surface and an outer surface, said membrane being configured and positioned such that:

an increase in pressure against the outer surface of said membrane will cause said membrane to move inwardly, thereby increasing the pressure of gas within said chamber and said lumen;

and a decrease in pressure against the outer surface of said membrane will allow said membrane to move outwardly, thereby decreasing the pressure of gas within said chamber and said lumen;

said gas filled lumen being thereby operable to transmit, in the proximal direction, changes in pressure exerted against the outer surface of said flaccid membrane; and said catheter further including a catheter-inflating connector apparatus connectable to said catheter, said apparatus being constructed such that connection of said catheter thereto will automatically cause a prescribed volume of gas to be entrapped within said catheter.

48. The catheter of claim 47 wherein said catheter inflating connector apparatus is further configured and constructed such that:

upon initial connection of said catheter to said pressure sensing apparatus, said apparatus will cause a first volume of gas to be contained within said catheter; and, upon subsequent disconnection and reconnection of said catheter to said pressure sensing apparatus, said coupling apparatus will cause a second volume of gas to be contained within said catheter.

49. A gas-column catheter for monitoring pressure within a mammalian body, said catheter comprising:

a catheter body having a proximal end, a distal end, and an outer surface; a gas-filled lumen extending longitudinally through at least a portion of said catheter body;

a gas-filled membrane-walled chamber at a fast location on said catheter body, said chamber being in gaseous communication with said lumen, said chamber being defined at least in part by a flaccid membrane having an inner surface and an outer surface, said membrane being configured and positioned such that:

an increase in pressure against the outer surface of said membrane will cause said membrane to move inwardly, thereby increasing the pressure of gas within said chamber and said lumen;

and a decrease in pressure against the outer surface of said membrane will allow said membrane to move outwardly, thereby decreasing the pressure of gas within said chamber and said lumen;

said gas filled lumen being thereby operable to transmit, in the proximal direction, changes in pressure exerted against the outer surface of said flaccid membrane; and said catheter further including a catheter-inflating apparatus for passing make-up gas into said gas filled lumen for replenishing gas which is lost from said catheter said apparatus including a diffusive make-up gas system coupled to said gas-filled lumen for replenishing gas which is lost from said catheter through outward diffusion, said diffusive make up gas system comprising a gas-filled reservoir containing gas at a pressure which exceeds the pressure of gas within the catheter lumen; a gas flow pathway through which gas may flow from said reservoir into said catheter lumen; and a membranous diffusion barrier disposed with said gas flow pathway such that gas flowing from said reservoir into said lumen must pass through said membranous barrier.

50. The catheter of claim 49 wherein the gas-filled reservoir of said diffusive make-up gas system further comprises:

a gas compressing apparatus for compressing gas within said reservoir.

51. The catheter of claim 49 wherein the rate of gas diffusion through the membranous diffusion barrier of the diffusive make-up gas system is matched to the diffusion characteristics of the flaccid membrane such that, at the time of connection the rate at which make-up gas will pass into the catheter lumen is substantially the same as the rate at which gas is lost from said catheter due to diffusion through said flaccid membrane.

52. The catheter of claim 49 wherein said diffusive make-up gas system is incorporated into a coupler to which said catheter may be coupled, said coupler being further constructed such that:

the act of coupling said catheter to said coupler will automatically result in entrapment of a preselected volume of gas within said catheter.

53. The catheter of claim 52 wherein said diffusive make-up gas system is further constructed such that:

the act of coupling said catheter to said coupler sensor will entrap and compress a quantity of gas within the gas-filled reservoir of said diffusive make up gas system.

54. A gas-column catheter insertable into a mammalian body for monitoring pressure changes within said mammalian body, said catheter comprising:

a catheter body having a proximal end, a distal end, and an outer surface having an outer diameter;

a gas-filled lumen extending longitudinally through said catheter body and terminating distally in an aperture at the distal end of said catheter body, said lumen being sized to contain therein a fixed volume of gas;

a first gas-filled membrane-walled chamber located on the distal end of said catheter body and in gaseous communication with said lumen through said aperture, said first membrane-walled chamber being defined at least in part by a bulbous membrane mounted on and extending distally from the distal end of said catheter body, said membrane having an outer surface and an inner surface, said membrane being flaccid and substantially non-elastic when in its fully gas-filled operative configuration, such that;

an increase in pressure against the outer surface of said membrane will compress said membrane causing a decrease in the volume of air within said chamber and a corresponding increase in the pressure of air within said lumen;

and a decrease in pressure against the outer surface of said membrane will allow said membrane to decompress, thereby causing an increase in the volume of air within said chamber and a corresponding decrease in the pressure of air within said lumen;

and said gas filled lumen being thereby operable to transmit, in the proximal direction, changes in pressure exerted against the outer surface of said flaccid membrane; and a catheter-inflating connector apparatus connectable to said catheter, said apparatus being constructed such that connection of said catheter thereto will automatically cause a prescribed volume of gas to be entrapped within said catheter.

55. A gas-column catheter insertable into a mammalian body for monitoring pressure changes within said mammalian body, said catheter comprising:

a catheter body having a proximal end, a distal end, and an outer surface having an outer diameter;

a gas-filled lumen extending longitudinally through said catheter body and terminating distally in an aperture at the distal end of said catheter body, said lumen being sized to contain therein a fixed volume of gas;

a fast gas-fried membrane-walled chamber located on the distal end of said catheter body and in gaseous communication with said lumen through said aperture, said first membrane-walled chamber being defined at least in part by a bulbous membrane mounted on and extending distally from the distal end of said catheter body, said membrane having an outer surface and an inner surface, said membrane being flaccid and substantially non-elastic when in its fully gas-filled operative configuration, such that;

an increase in pressure against the outer surface of said membrane will compress said membrane causing a decrease in the volume of air within said chamber and a corresponding increase in the pressure of air within said lumen;

and a decrease in pressure against the outer surface of said membrane will allow said membrane to decompress, thereby causing an increase in the volume of air within said chamber and a corresponding decrease in the pressure of air within said lumen;

and said gas filled lumen being thereby operable to transmit, in the proximal direction, changes in pressure exerted against the outer surface of said flaccid membrane; and an apparatus for passing make-up gas into said gas-filled lumen for replenishing gas which is lost from said catheter, said apparatus including it diffusive make-up gas system coupled to said gas-filled lumen for replenishing gas which is lost from said catheter through outward diffusion, said diffusive make up gas system comprising a gas-filled reservoir containing gas at a pressure which exceeds the pressure of gas within the catheter lumen; a gas flow pathway through which gas may flow from said reservoir into said catheter lumen; and a membranous diffusion barrier disposed within said gas flow pathway such that gas flowing from said reservoir into said lumen must pass through said membranous barrier.

* * * * *